(12) United States Patent
Chung et al.

(10) Patent No.: US 10,980,477 B2
(45) Date of Patent: Apr. 20, 2021

(54) ELECTRONIC DEVICE AND METHOD FOR PROVIDING DIGESTIBILITY ON EATEN FOOD

(71) Applicant: Samsung Electronics Co., Ltd., Gyeonggi-do (KR)

(72) Inventors: So Hyun Chung, Seoul (KR); Gitae Mun, Gyeonggi-do (KR); Jeong-Min Park, Gyeonggi-do (KR); Seung-Eun Lee, Seoul (KR); Sun Ok Jung, Gyeonggi-do (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 120 days.

(21) Appl. No.: 16/033,293

(22) Filed: Jul. 12, 2018

(65) Prior Publication Data
US 2019/0015041 A1 Jan. 17, 2019

(30) Foreign Application Priority Data

Jul. 13, 2017 (KR) .................. 10-2017-0088823

(51) Int. Cl.
*G16H 20/60* (2018.01)
*A61B 5/0205* (2006.01)
(Continued)

(52) U.S. Cl.
CPC .......... *A61B 5/4866* (2013.01); *A61B 5/0205* (2013.01); *A61B 5/4815* (2013.01);
(Continued)

(58) Field of Classification Search
CPC ..... A61B 5/4866; A61B 5/742; A61B 5/4815; A61B 5/0205; A61B 5/1118;
(Continued)

(56) References Cited

U.S. PATENT DOCUMENTS

2014/0275852 A1* 9/2014 Hong .................. A61B 5/0002
600/301
2015/0132722 A1* 5/2015 Menczel ............... A61B 5/1118
434/127
(Continued)

FOREIGN PATENT DOCUMENTS

EP  3 061 390 A1  8/2016
EP  3 132 740 A1  2/2017
(Continued)

OTHER PUBLICATIONS

European Search Report dated Dec. 5, 2018.
(Continued)

*Primary Examiner* — William J Levicky
*Assistant Examiner* — Alexander M Eisenberg
(74) *Attorney, Agent, or Firm* — Cha & Reiter, LLC

(57) ABSTRACT

A wearable device according to various embodiments may include a biometric sensor, an output device, and a processor operatively coupled with the biometric sensor and the output device, and configured to obtain food intake information of a user corresponding to the wearable device, to obtain biometric information of the user by using the biometric sensor, to identify a digestibility of the food of the user, based at least in part on a change of the biometric information corresponding to the food intake information, and to provide information of the digestibility, using the output device.

18 Claims, 22 Drawing Sheets

(51) Int. Cl.
　　　*A61B 5/00*　　(2006.01)
　　　*A61B 5/024*　(2006.01)
　　　*A61B 5/11*　　(2006.01)
(52) U.S. Cl.
　　　CPC ............. *A61B 5/742* (2013.01); *G16H 20/60*
　　　　　(2018.01); *A61B 5/02405* (2013.01); *A61B*
　　　　　*5/02416* (2013.01); *A61B 5/02438* (2013.01);
　　　　　　　　　　　　　　　*A61B 5/1118* (2013.01)
(58) Field of Classification Search
　　　CPC ............ A61B 5/02438; A61B 5/02416; A61B
　　　　　　　　　　　　　　　5/02405; G16H 20/60
　　　USPC .......................................... 600/301; 434/127
　　　See application file for complete search history.

(56)　　　　　　　　References Cited

U.S. PATENT DOCUMENTS

| | | | | |
|---|---|---|---|---|
| 2015/0351681 | A1* | 12/2015 | Lee | A61B 5/7282 600/595 |
| 2015/0364057 | A1* | 12/2015 | Catani | G09B 19/0092 434/127 |
| 2016/0148535 | A1* | 5/2016 | Ashby | G09B 19/0092 434/127 |
| 2016/0166195 | A1* | 6/2016 | Radecka | A61B 5/486 434/127 |
| 2016/0324487 | A1* | 11/2016 | Guo | A61B 5/0816 |
| 2016/0328991 | A1* | 11/2016 | Simpson | A61B 5/7435 |
| 2017/0042485 | A1 | 2/2017 | Chung et al. | |

FOREIGN PATENT DOCUMENTS

| | | |
|---|---|---|
| EP | 3 354 193 A1 | 8/2018 |
| IN | 201747005402 | 4/2017 |
| KR | 10-2017-0019745 A | 2/2017 |
| WO | 2017/026680 A1 | 2/2017 |
| WO | 2017/051442 A1 | 3/2017 |

OTHER PUBLICATIONS

Lilian C. M. Vloet et al., "The Effect of Meals at Different Mealtimes on Blood Pressure and Systoms in Geriatric Patients With Postprandial Hypotension", Journal of Gerontology: Medical Sciences 2003, vol. 58A, No. 11, pp. 1031-1035.

Siri Marte Hollekim-Strand et al., "Fast food increases postprandial cardiac workload in type 2 diabetes independent of pre-exercise: A pilot study", Nutrition Journal (2015).

Fiona E. Lithander et al., "Postprandial effect of dietary fat quantity and quality on arterial stiffness and wave reflection: a randomised controlled trial", Nutrition Journal, 2013, 8 pages, http://www.nutritionj.com/content/12/1/93.

European Search Report dated Nov. 20, 2019.

* cited by examiner

ELECTRONIC DEVICE AND METHOD FOR PROVIDING DIGESTIBILITY ON EATEN FOOD

CROSS-REFERENCE TO RELATED APPLICATION(S)

This application is based on and claims priority under 35 U.S.C. § 119 to Korean Patent Application No. 10-2017-0088823, filed on Jul. 13, 2017, in the Korean Intellectual Property Office, the disclosure of which is incorporated by reference herein in its entirety.

TECHNICAL FIELD

The present disclosure relates to an electronic device and a method for providing a digestibility of a food eaten.

BACKGROUND

Based on growing interest in health, an electronic device including a biometric sensor is under development. Such an electronic device may obtain state information of a human body and thus provide health information.

SUMMARY

According to various embodiments, a wearable device may include a biometric sensor, an output device, and a processor operatively coupled with the biometric sensor and the output device, and configured to obtain food intake information of a user corresponding to the wearable device, to obtain biometric information of the user by using the biometric sensor, to identify a digestibility of the food of the user, based at least in part on a change of the biometric information corresponding to the food intake information, and to provide information of the digestibility, using the output device.

According to various embodiments, a wearable device may include a housing, a display disposed in a first area of the housing, one or more sensors electrically connected to one or more terminals contactable to part of a user body through a second area of the housing, a memory storing instructions, and one or more processors operably coupled with the memory, the one or more sensors, and the display, and configured to execute the stored instructions to obtain resting heart rate information of the user through the one or more sensor, to determine user food intake, based at least in part on the obtained resting heart rate information, to identify, in response to the determination, a change of the resting heart rate from the obtained resting heart rate information, to determine a digestibility of the food taken by the user, based on the change of the resting heart rate, and to store the digestibility information in the memory.

According to various embodiments, an electronic device may include a communication interface, an output device, and one or more processors operably coupled with the communication interface and the output device and configured to obtain information of a food taken by a user of the electronic device, to obtain information of a resting heart rate of the user from a wearable device associated with the electronic device, to determine a digestibility of the food based at least in part on the food information and the resting heart rate information, and to provide digestibility information.

According to various embodiments, a method of a wearable device may include obtaining food intake information of a user corresponding to the wearable device, obtaining biometric information of the user by using the biometric sensor, identifying a digestibility of the food of the user, based at least in part on a change of the biometric information corresponding to the food intake information, and providing information of the digestibility, using the output device.

According to various embodiments, a method of a wearable device may include obtaining resting heart rate information of the user through the one or more sensor, determining user food intake, based at least in part on the obtained resting heart rate information, identifying, in response to the determination, a change of the resting heart rate from the obtained resting heart rate information, determining a digestibility of the food taken by the user, based on the change of the resting heart rate, and storing the digestibility information in the memory.

According to various embodiments, a method of an electronic device may include obtaining information of a food taken by a user of the electronic device, obtaining information of a resting heart rate of the user from a wearable device associated with the electronic device, determining a digestibility of the food based at least in part on the food information and the resting heart rate information, and providing digestibility information.

Other aspects, advantages, and salient features of the disclosure will become apparent to those skilled in the art from the following detailed description, which, taken in conjunction with the annexed drawings, discloses various embodiments of the disclosure.

BRIEF DESCRIPTION OF THE DRAWINGS

The above and other aspects, features, and advantages of certain embodiments of the present disclosure will be more apparent from the following description taken in conjunction with the accompanying drawings, in which.

Throughout the drawings, like reference numerals will be understood to refer to like parts, components and structures.

DETAILED DESCRIPTION

Figure 1:
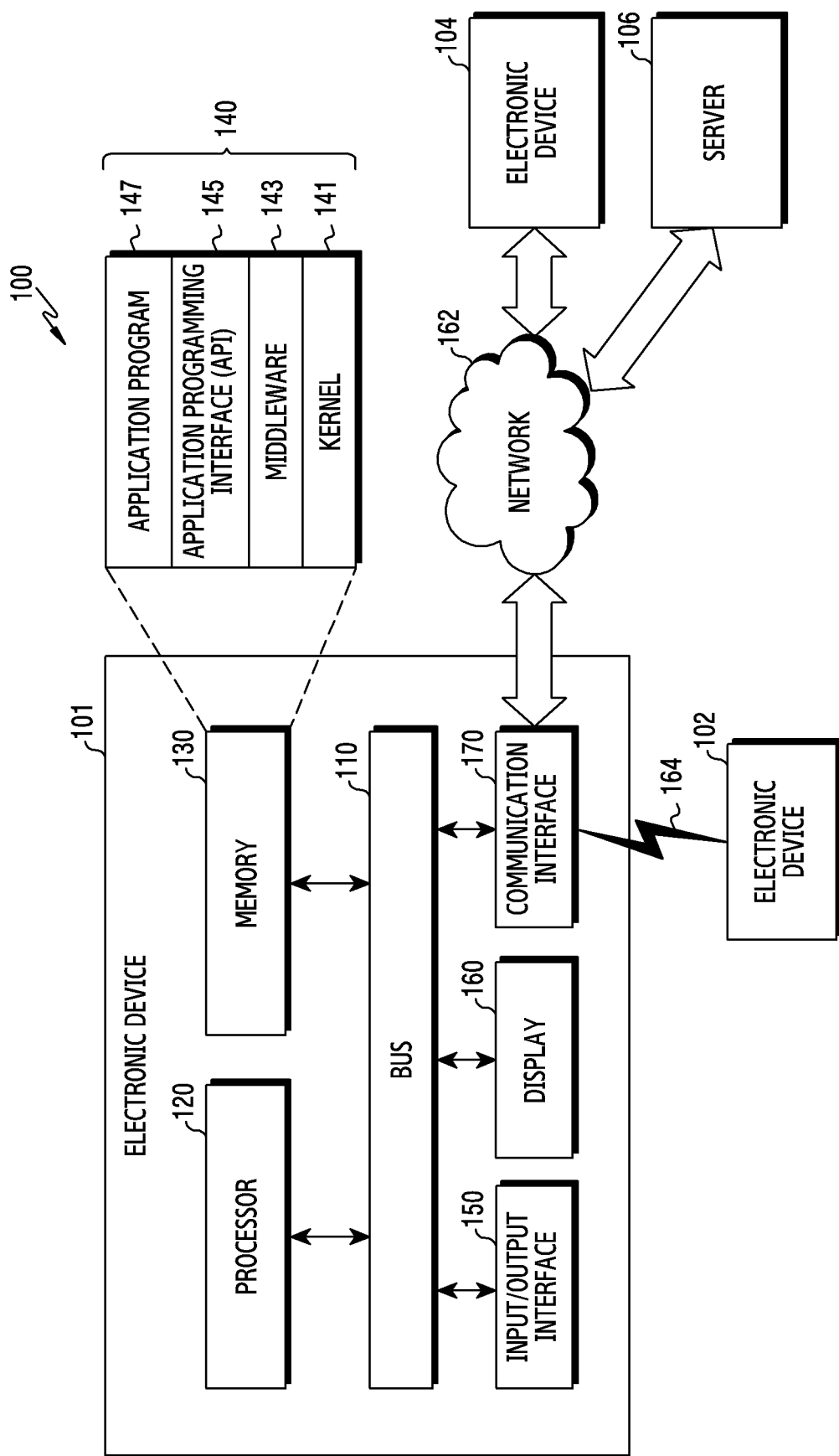
FIG. 1 illustrates a network environment including an electronic device according to various embodiments.

Hereinafter, various embodiments of the present disclosure will be described with reference to the accompanying drawings. However, it should be understood that there is no intent to limit the present disclosure to the particular forms disclosed herein; rather, the present disclosure should be construed to cover various modifications, equivalents, and/or alternatives of embodiments of the present disclosure. In describing the drawings, similar reference numerals may be used to designate similar constituent elements.

As used herein, the expression "have", "may have", "include", or "may include" refers to the existence of a corresponding feature (e.g., numeral, function, operation, or constituent element such as component), and does not exclude one or more additional features.

In the present disclosure, the expression "A or B", "at least one of A or/and B", or "one or more of A or/and B" may include all possible combinations of the items listed. For example, the expression "A or B", "at least one of A and B", or "at least one of A or B" refers to all of (1) including at least one A, (2) including at least one B, or (3) including all of at least one A and at least one B.

The expression "a first", "a second", "the first", or "the second" used in various embodiments of the present disclosure may modify various components regardless of the order and/or the importance but does not limit the corresponding components. For example, a first user device and a second user device indicate different user devices although both of them are user devices. For example, a first element may be termed a second element, and similarly, a second element may be termed a first element without departing from the scope of the present disclosure.

It should be understood that when an element (e.g., first element) is referred to as being (operatively or communicatively) "connected," or "coupled," to another element (e.g., second element), it may be directly connected or coupled directly to the other element or any other element (e.g., third element) may be interposer between them. In contrast, it may be understood that when an element (e.g., first element) is referred to as being "directly connected," or "directly coupled" to another element (second element), there are no element (e.g., third element) interposed between them.

The expression "configured to" used in the present disclosure may be exchanged with, for example, "suitable for", "having the capacity to", "designed to", "adapted to", "made to", or "capable of" according to the situation. The term "configured to" may not necessarily imply "specifically designed to" in hardware. Alternatively, in some situations, the expression "device configured to" may mean that the device, together with other devices or components, "is able to". For example, the phrase "processor adapted (or configured) to perform A, B, and C" may mean a dedicated processor (e.g. embedded processor) for performing the corresponding operations or a generic-purpose processor (e.g., central processing unit (CPU) or application processor (AP)) that can perform the corresponding operations by executing one or more software programs stored in a memory device.

The terms used in the present disclosure are only used to describe specific embodiments, and are not intended to limit the present disclosure. As used herein, singular forms may include plural forms as well unless the context clearly indicates otherwise. Unless defined otherwise, all terms used herein, including technical and scientific terms, have the same meaning as those commonly understood by a person skilled in the art to which the present disclosure pertains. Such terms as those defined in a generally used dictionary may be interpreted to have the meanings equal to the contextual meanings in the relevant field of art, and are not to be interpreted to have ideal or excessively formal meanings unless clearly defined in the present disclosure. In some cases, even the term defined in the present disclosure should not be interpreted to exclude embodiments of the present disclosure.

An electronic device according to various embodiments of the present disclosure may include at least one of, for example, a smart phone, a tablet Personal Computer (PC), a mobile phone, a video phone, an electronic book reader (e-book reader), a desktop PC, a laptop PC, a netbook computer, a workstation, a server, a Personal Digital Assistant (PDA), a Portable Multimedia Player (PMP), a MPEG-1 audio layer-3 (MP3) player, a mobile medical device, a camera, and a wearable device. According to various embodiments, the wearable device may include at least one of an accessory type (e.g., a watch, a ring, a bracelet, an anklet, a necklace, a glasses, a contact lens, or a Head-Mounted Device (HMD)), a fabric or clothing integrated type (e.g., an electronic clothing), a body-mounted type (e.g., a skin pad, or tattoo), and a bio-implantable type (e.g., an implantable circuit).

According to some embodiments, the electronic device may be a home appliance. The home appliance may include at least one of, for example, a television, a Digital Video Disk (DVD) player, an audio, a refrigerator, an air conditioner, a vacuum cleaner, an oven, a microwave oven, a washing machine, an air cleaner, a set-top box, a home automation control panel, a security control panel, a TV box (e.g., Samsung HomeSync®, Apple TV®, or Google TV®), a game console (e.g., Xbox® and PlayStation®), an electronic dictionary, an electronic key, a camcorder, and an electronic photo frame.

According to another embodiment, the electronic device may include at least one of various medical devices (e.g., various portable medical measuring devices (a blood glucose monitoring device, a heart rate monitoring device, a blood pressure measuring device, a body temperature measuring device, etc.), a Magnetic Resonance Angiography (MRA), a Magnetic Resonance Imaging (MRI), a Computed Tomography (CT) machine, and an ultrasonic machine), a navigation device, a Global Positioning System (GPS) receiver, an Event Data Recorder (EDR), a Flight Data Recorder (FDR), a Vehicle Infotainment Devices, an electronic devices for a ship (e.g., a navigation device for a ship, and a gyro-compass), avionics, security devices, an automotive head unit, a robot for home or industry, an automatic teller's machine (ATM) in banks, point of sales (POS) in a shop, or internet device of things (e.g., a light bulb, various sensors, electric or gas meter, a sprinkler device, a fire alarm, a thermostat, a streetlamp, a toaster, a sporting goods, a hot water tank, a heater, a boiler, etc.).

According to some embodiments, the electronic device may include at least one of a part of furniture or a building/structure, an electronic board, an electronic signature receiving device, a projector, and various kinds of measuring instruments (e.g., a water meter, an electric meter, a gas meter, and a radio wave meter). The electronic device according to various embodiments of the present disclosure may be a combination of one or more of the aforementioned various devices. The electronic device according to some embodiments of the present disclosure may be a flexible device. Further, the electronic device according to an embodiment of the present disclosure is not limited to the aforementioned devices, and may include a new electronic device according to the development of technology.

Hereinafter, an electronic device according to various embodiments will be described with reference to the accompanying drawings. As used herein, the term "user" may indicate a person who uses an electronic device or a device (e.g., an artificial intelligence electronic device) that uses an electronic device.

FIG. 1 illustrates a network environment including an electronic device according to various embodiments of the present disclosure.

An electronic device 101 within a network environment, according to various embodiments, will be described with reference to FIG. 1. The electronic device 101 may include a bus 110, a processor 120, a memory 130, an input/output interface 150, a display 160, and a communication interface 170. According to an embodiment of the present disclosure, the electronic device 101 may omit at least one of the above components or may further include other components.

In certain embodiments, the processor 120 can be configured to obtain food intake information of a user, obtain biometric information of the user, and determine the digestibility of the food based at least in biometric information, such as a resting heart rate.

The display 160 can provide information of the digestibility, determined by the processor using a user interface.

The bus 110 may include, for example, a circuit which interconnects the components 110 to 170 and delivers a communication (e.g., a control message and/or data) between the components 110 to 170.

The processor 120 may include one or more of a Central Processing Unit (CPU), an Application Processor (AP), and a Communication Processor (CP). The processor 120 may carry out, for example, calculation or data processing relating to control and/or communication of at least one other component of the electronic device 101.

The memory 130 may include a volatile memory and/or a non-volatile memory. The memory 130 may store, for example, commands or data relevant to at least one other component of the electronic device 101. According to an embodiment of the present disclosure, the memory 130 may store software and/or a program 140. The program 140 may include, for example, a kernel 141, middleware 143, an Application Programming Interface (API) 145, and/or application programs (or "applications") 147. At least some of the kernel 141, the middleware 143, and the API 145 may be referred to as an Operating System (OS).

In certain embodiments, the memory 130 can store previous measurements of digestibility of food, based on type of food, place the food was obtained, and digestibility of food by different users of the electronic device.

The kernel 141 may control or manage system resources (e.g., the bus 110, the processor 120, or the memory 130) used for performing an operation or function implemented in the other programs (e.g., the middleware 143, the API 145, or the application programs 147). Furthermore, the kernel 141 may provide an interface through which the middleware 143, the API 145, or the application programs 147 may access the individual components of the electronic device 101 to control or manage the system resources.

The middleware 143, for example, may serve as an intermediary for allowing the API 145 or the application programs 147 to communicate with the kernel 141 to exchange data.

Also, the middleware 143 may process one or more task requests received from the application programs 147 according to priorities thereof. For example, the middleware 143 may assign priorities for using the system resources (e.g., the bus 110, the processor 120, the memory 130, or the like) of the electronic device 101, to at least one of the application programs 147. For example, the middleware 143 may perform scheduling or loading balancing on the one or more task requests by processing the one or more task requests according to the priorities assigned thereto.

The API 145 is an interface through which the applications 147 control functions provided from the kernel 141 or the middleware 143, and may include, for example, at least one interface or function (e.g., instruction) for file control, window control, image processing, character control, and the like.

The input/output interface 150, for example, may function as an interface that may transfer commands or data input from a user or another external device to the other element(s) of the electronic device 101. Furthermore, the input/output interface 150 may output the commands or data received from the other element(s) of the electronic device 101 to the user or another external device.

Examples of the display 160 may include a Liquid Crystal Display (LCD), a Light-Emitting Diode (LED) display, an Organic Light-Emitting Diode (OLED) display, a Micro-ElectroMechanical Systems (MEMS) display, and an electronic paper display. The display 160 may display, for example, various types of contents (e.g., text, images, videos, icons, or symbols) to users. The display 160 may include a touch screen, and may receive, for example, a touch, gesture, proximity, or hovering input using an electronic pen or a user's body part.

The communication interface 170 may establish communication, for example, between the electronic device 101 and an external device (e.g., a first external electronic device 102, a second external electronic device 104, or a server 106). For example, the communication interface 170 may be connected to a network 162 through wireless or wired communication, and may communicate with an external device (e.g., the second external electronic device 104 or the server 106). The wireless communication may use at least one of, for example, Long Term Evolution (LTE), LTE-Advance (LTE-A), Code Division Multiple Access (CDMA), Wideband CDMA (WCDMA), Universal Mobile Telecommunications System (UMTS), Wireless Broadband (WiBro), and Global System for Mobile Communications (GSM), as a cellular communication protocol. In addition, the wireless communication may include, for example, short range communication 164. The short-range communication 164 may include at least one of, for example, Wi-Fi, Bluetooth, Near Field Communication (NFC), and Global Navigation Satellite System (GNSS). GNSS may include, for example, at least one of global positioning system (GPS), global navigation satellite system (Glonass), Beidou Navigation satellite system (Beidou) or Galileo, and the European global satellite-based navigation system, based on a location, a bandwidth, or the like. Hereinafter, in the present disclosure, the "GPS" may be interchangeably used with the "GNSS". The wired communication may include, for example, at least one of a Universal Serial Bus (USB), a High Definition Multimedia Interface (HDMI), Recommended Standard 232 (RS-232), and a Plain Old Telephone Service (POTS). The network 162 may include at least one of a telecommunication network such as a computer network (e.g., a LAN or a WAN), the Internet, and a telephone network.

The communication interface 170 can be used to determine information about the food consumed by the user, by identifying the location of the electronic device based on GPS positioning, identification of present Wi-Fi networks, and identification of point of sale networks for NFC, to name a few.

Each of the first and second external electronic devices 102 and 104 may be of a type identical to or different from that of the electronic device 101. According to an embodiment of the present disclosure, the server 106 may include a group of one or more servers.

In certain embodiments, the electronic device 101 can transmit digestibility information to external electronic devices 102.

According to various embodiments of the present disclosure, all or some of the operations performed in the electronic device 101 may be executed in another electronic device or a plurality of electronic devices (e.g., the electronic devices 102 and 104 or the server 106). According to an embodiment of the present disclosure, when the electronic device 101 has to perform some functions or services automatically or in response to a request, the electronic device 101 may request another device (e.g., the electronic device 102 or 104 or the server 106) to execute at least some functions relating thereto instead of or in addition to autonomously performing the functions or services. Another electronic device (e.g., the electronic device 102 or 104, or the server 106) may execute the requested functions or the additional functions, and may deliver a result of the execution to the electronic device 101. The electronic device 101 may process the received result as it is or additionally, and may provide the requested functions or services. To this end, for example, cloud computing, distributed computing, or client-server computing technologies may be used.

In various embodiments, if the electronic device 101 is a wearable device, the first external electronic device 102 may be associated with the electronic device 101. For example, the first external electronic device 102 may be a smart phone associated with the electronic device 101 which is the wearable device. In various embodiments, if the electronic device 101 is a smart phone, the first external electronic device 102 may be a wearable device associated with the electronic device 101.

Figure 2:
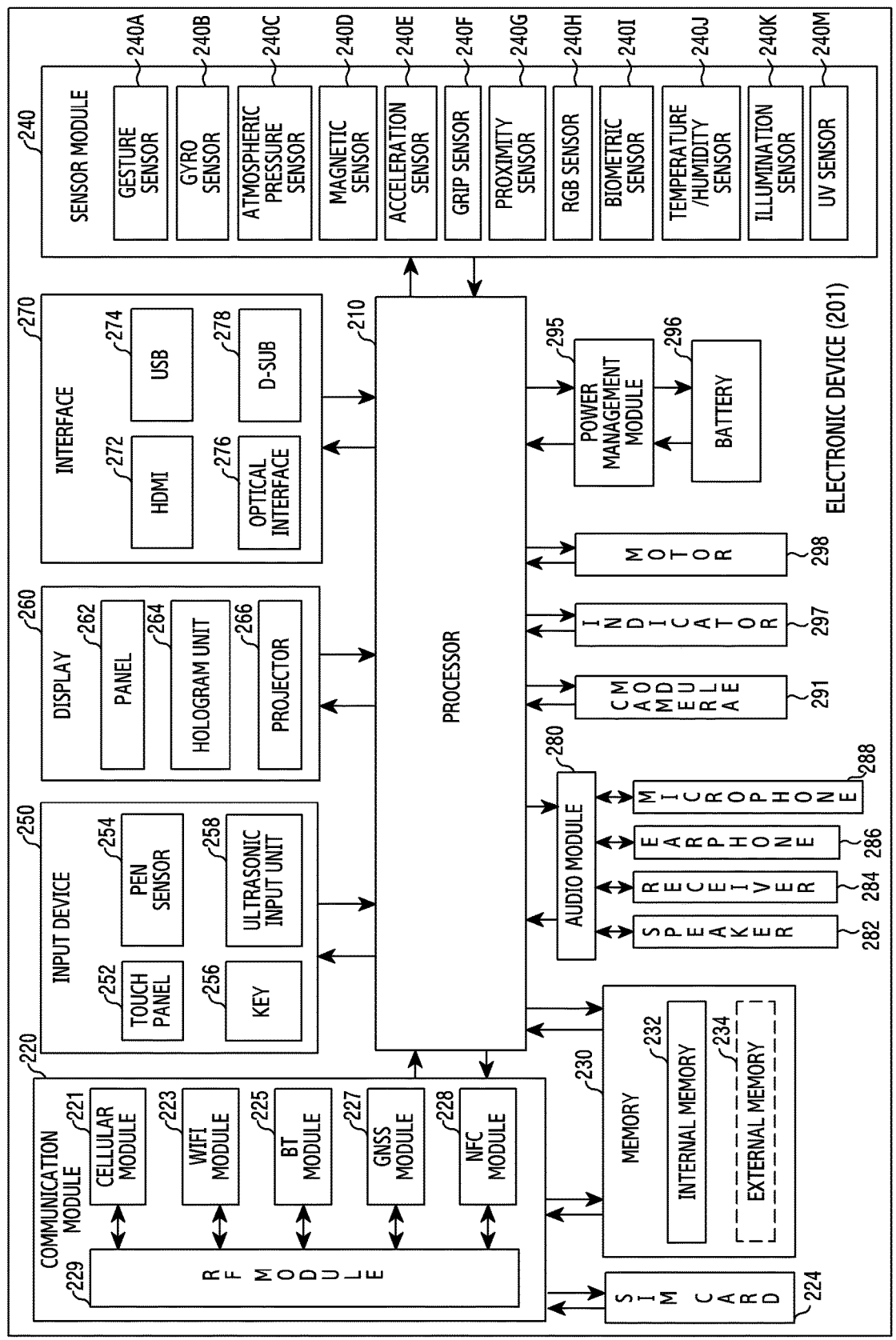
FIG. 2 illustrates a block diagram of an electronic device according to various embodiments.

FIG. 2 is a block diagram of an electronic device according to various embodiments of the present disclosure.

The electronic device 201 may include, for example, all or a part of the electronic device 101 shown in FIG. 1. The electronic device 201 may include one or more processors 210 (e.g., Application Processors (AP)), a communication module 220, a Subscriber Identification Module (SIM) 224, a memory 230, a sensor module 240, an input device 250, a display 260, an interface 270, an audio module 280, a camera module 291, a power management module 295, a battery 296, an indicator 297, and a motor 298.

The processor 210 may control a plurality of hardware or software components connected to the processor 210 by driving an operating system or an application program, and perform processing of various pieces of data and calculations. The processor 210 may be embodied as, for example, a System on Chip (SoC). According to an embodiment of the present disclosure, the processor 210 may further include a Graphic Processing Unit (GPU) and/or an image signal processor. The processor 210 may include at least some (for example, a cellular module 221) of the components illustrated in FIG. 2. The processor 210 may load, into a volatile memory, commands or data received from at least one (e.g., a non-volatile memory) of the other components and may process the loaded commands or data, and may store various data in a non-volatile memory.

The communication module 220 may have a configuration equal or similar to that of the communication interface 170 of FIG. 1. The communication module 220 may include, for example, a cellular module 221, a Wi-Fi module 223, a BT module 225, a GNSS module 227 (e.g., a GPS module 227, a Glonass module, a Beidou module, or a Galileo module), an NFC module 228, and a Radio Frequency (RF) module 229.

The cellular module 221, for example, may provide a voice call, a video call, a text message service, or an Internet service through a communication network. According to an embodiment of the present disclosure, the cellular module 221 may distinguish and authenticate the electronic device 201 in a communication network using the subscriber identification module 224 (for example, the SIM card). According to an embodiment of the present disclosure, the cellular module 221 may perform at least some of the functions that the AP 210 may provide. According to an embodiment of the present disclosure, the cellular module 221 may include a communication processor (CP).

For example, each of the Wi-Fi module 223, the BT module 225, the GNSS module 227, and the NFC module 228 may include a processor for processing data transmitted/received through a corresponding module. According to an embodiment of the present disclosure, at least some (e.g., two or more) of the cellular module 221, the Wi-Fi module 223, the BT module 225, the GNSS module 227, and the NFC module 228 may be included in one Integrated Chip (IC) or IC package.

The RF module 229, for example, may transmit/receive a communication signal (e.g., an RF signal). The RF module 229 may include, for example, a transceiver, a Power Amplifier Module (PAM), a frequency filter, a Low Noise Amplifier (LNA), and an antenna. According to another embodiment of the present disclosure, at least one of the cellular module 221, the WIFI module 223, the BT module 225, the GNSS module 227, and the NFC module 228 may transmit/receive an RF signal through a separate RF module.

The subscriber identification module 224 may include, for example, a card including a subscriber identity module and/or an embedded SIM, and may contain unique identification information (e.g., an Integrated Circuit Card Identifier (ICCID)) or subscriber information (e.g., an International Mobile Subscriber Identity (IMSI)).

The memory 230 (e.g., the memory 130) may include, for example, an embedded memory 232 or an external memory 234. The embedded memory 232 may include at least one of a volatile memory (e.g., a Dynamic Random Access Memory (DRAM), a Static RAM (SRAM), a Synchronous Dynamic RAM (SDRAM), and the like) and a non-volatile memory (e.g., a One Time Programmable Read Only Memory (OTPROM), a Programmable ROM (PROM), an Erasable and Programmable ROM (EPROM), an Electrically Erasable and Programmable ROM (EEPROM), a mask ROM, a flash ROM, a flash memory (e.g., a NAND flash memory or a NOR flash memory), a hard disc drive, a Solid State Drive (SSD), and the like).

The external memory 234 may further include a flash drive, for example, a Compact Flash (CF), a Secure Digital (SD), a Micro Secure Digital (Micro-SD), a Mini Secure Digital (Mini-SD), an eXtreme Digital (xD), a MultiMediaCard (MMC), a memory stick, or the like. The external memory 234 may be functionally and/or physically connected to the electronic device 201 through various interfaces.

The sensor module 240, for example, may measure a physical quantity or detect an operation state of the electronic device 201, and may convert the measured or detected information into an electrical signal. The sensor module 240 may include, for example, at least one of a gesture sensor 240A, a gyro sensor 240B, an atmospheric pressure sensor (barometer) 240C, a magnetic sensor 240D, an acceleration sensor 240E, a grip sensor 240F, a proximity sensor 240G, a color sensor 240H (e.g., red, green, and blue (RGB) sensor), a biometric sensor (medical sensor) 240I, a temperature/humidity sensor 240J, an illuminance sensor 240K, and a Ultra Violet (UV) sensor 240M and a Time of Flight sensor (240). Additionally or alternatively, the sensor module 240 may include, for example, an E-nose sensor, an electromyography (EMG) sensor, an electroencephalogram (EEG) sensor, an electrocardiogram (ECG) sensor, an Infrared (IR) sensor, an iris scan sensor, and/or a finger scan sensor. The sensor module 240 may further include a control circuit for controlling one or more sensors included therein. According to an embodiment of the present disclosure, the electronic device 201 may further include a processor configured to control the sensor module 240, as a part of the processor 210 or separately from the processor 210, and may control the sensor module 240 while the processor 210 is in a sleep state.

In certain embodiments, the biometric sensor 240I can include a ppg (photoplethysmogram) sensor for measuring the resting heart rate (RHR). The RHR can be used for determining digestibility of food consumed by the user. The ppg sensor may also measure blood pressure or glucose. The biometric sensor 240I can include a glucometer.

The input device 250 may include, for example, a touch panel 252, a (digital) pen sensor 254, a key 256, or an ultrasonic input device 258. The touch panel 252 may use, for example, at least one of a capacitive type, a resistive type, an infrared type, and an ultrasonic type. The touch panel 252 may further include a control circuit. The touch panel 252 may further include a tactile layer, and provide a tactile reaction to the user.

The (digital) pen sensor 254 may include, for example, a recognition sheet which is a part of the touch panel or is separated from the touch panel. The key 256 may include, for example, a physical button, an optical key or a keypad. The ultrasonic input device 258 may detect, through a microphone (e.g., the microphone 288), ultrasonic waves generated by an input tool, and identify data corresponding to the detected ultrasonic waves.

The display 260 (e.g., the display 160) may include a panel 262, a hologram device 264, or a projector 266. The panel 262 may include a configuration identical or similar to the display 160 illustrated in FIG. 1. The panel 262 may be implemented to be, for example, flexible, transparent, or wearable. The panel 262 may be embodied as a single module with the touch panel 252. The hologram device 264 may show a three dimensional (3D) image in the air by using an interference of light. The projector 266 may project light onto a screen to display an image. The screen may be located, for example, in the interior of or on the exterior of the electronic device 201. According to an embodiment of the present disclosure, the display 260 may further include a control circuit for controlling the panel 262, the hologram device 264, or the projector 266.

The interface 270 may include, for example, a High-Definition Multimedia Interface (HDMI) 272, a Universal Serial Bus (USB) 274, an optical interface 276, or a D-sub-miniature (D-sub) 278. The interface 270 may be included in, for example, the communication interface 170 illustrated in FIG. 1. Additionally or alternatively, the interface 270 may include, for example, a Mobile High-definition Link (MHL) interface, a Secure Digital (SD) card/Multi-Media Card (MMC) interface, or an Infrared Data Association (IrDA) standard interface.

The audio module 280, for example, may bilaterally convert a sound and an electrical signal. At least some components of the audio module 280 may be included in, for example, the input/output interface 150 illustrated in FIG. 1. The audio module 280 may process voice information input or output through, for example, a speaker 282, a receiver 284, earphones 286, or the microphone 288.

The camera module 291 is, for example, a device which may photograph a still image and a video. According to an embodiment of the present disclosure, the camera module 291 may include one or more image sensors (e.g., a front sensor or a back sensor), a lens, an Image Signal Processor (ISP) or a flash (e.g., LED or xenon lamp).

The power management module 295 may manage, for example, power of the electronic device 201. According to an embodiment of the present disclosure, the power management module 295 may include a Power Management Integrated Circuit (PMIC), a charger Integrated Circuit (IC), or a battery or fuel gauge. The PMIC may use a wired and/or wireless charging method. Examples of the wireless charging method may include, for example, a magnetic resonance method, a magnetic induction method, an electromagnetic wave method, and the like. Additional circuits (e.g., a coil loop, a resonance circuit, a rectifier, etc.) for wireless charging may be further included. The battery gauge may measure, for example, a residual quantity of the battery 296, and a voltage, a current, or a temperature while charging. The battery 296 may include, for example, a rechargeable battery and/or a solar battery.

The indicator 297 may display a particular state (e.g., a booting state, a message state, a charging state, or the like) of the electronic device 201 or a part (e.g., the processor 210) of the electronic device 201. The motor 298 may convert an electrical signal into a mechanical vibration, and may generate a vibration, a haptic effect, or the like. Although not illustrated, the electronic device 201 may include a processing device (e.g., a GPU) for supporting a mobile TV. The processing device for supporting a mobile TV may process, for example, media data according to a certain standard such as Digital Multimedia Broadcasting (DMB), Digital Video Broadcasting (DVB), or mediaFLO®.

Each of the above-described component elements of hardware according to the present disclosure may be configured with one or more components, and the names of the corresponding component elements may vary based on the type of electronic device. In various embodiments, the electronic device may include at least one of the above-described elements. Some of the above-described elements may be omitted from the electronic device, or the electronic device may further include additional elements. Also, some of the hardware components according to various embodiments may be combined into one entity, which may perform functions identical to those of the relevant components before the combination.

Figure 3:
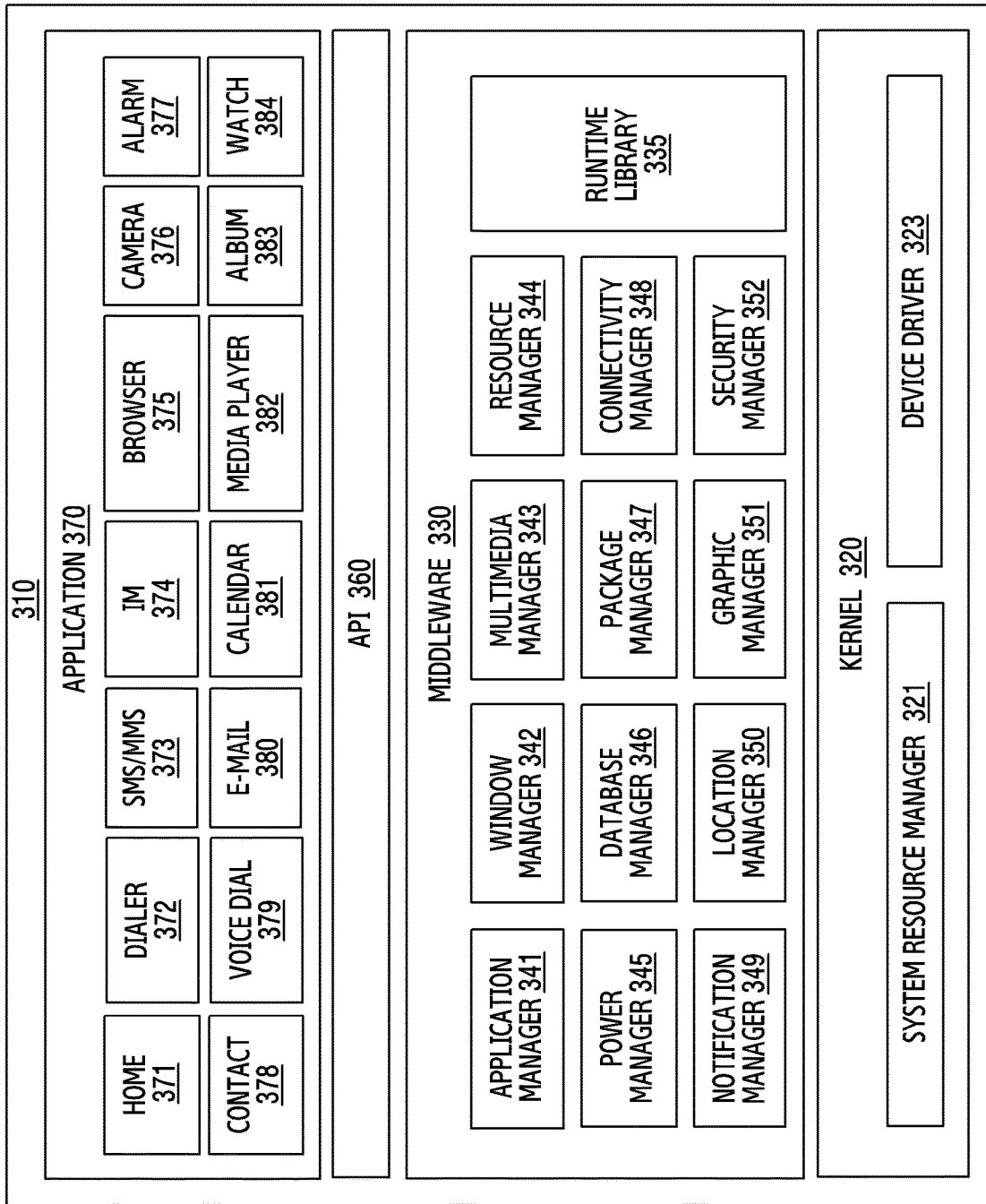
FIG. 3 illustrates a block diagram of a program module according to various embodiments.

FIG. 3 is a block diagram of a program module according to various embodiments of the present disclosure.

According to an embodiment of the present disclosure, the program module 310 (e.g., the program 140) may include an Operating System (OS) for controlling resources related to the electronic device (e.g., the electronic device 101) and/or various applications (e.g., the application programs 147) executed in the operating system. The operating system may be, for example, Android®, iOS®, Windows®, Symbian®, Tizen®, Bada®, or the like.

The program module 310 may include a kernel 320, middleware 330, an API 360, and/or applications 370. At least some of the program module 310 may be preloaded on an electronic device, or may be downloaded from an external electronic device (e.g., the electronic device 102 or 104, or the server 106).

The kernel 320 (e.g., the kernel 141) may include, for example, a system resource manager 321 and/or a device driver 323. The system resource manager 321 may control, allocate, or collect system resources. According to an embodiment of the present disclosure, the system resource manager 321 may include a process management unit, a memory management unit, a file system management unit, and the like. The device driver 323 may include, for example, a display driver, a camera driver, a Bluetooth® driver, a shared memory driver, a USB driver, a keypad driver, a Wi-Fi driver, an audio driver, or an Inter-Process Communication (IPC) driver.

For example, the middleware 330 may provide a function required in common by the applications 370, or may provide various functions to the applications 370 through the API 360 so as to enable the applications 370 to efficiently use the limited system resources in the electronic device. According to an embodiment of the present disclosure, the middleware 330 (e.g., the middleware 143) may include at least one of a run time library 335, an application manager 341, a window manager 342, a multimedia manager 343, a resource manager 344, a power manager 345, a database manager 346, a package manager 347, a connectivity manager 348, a notification manager 349, a location manager 350, a graphic manager 351, and a security manager 352.

The runtime library 335 may include a library module that a compiler uses in order to add a new function through a programming language while an application 370 is being executed. The runtime library 335 may perform input/output management, memory management, the functionality for an arithmetic function, or the like.

The application manager 341 may manage, for example, a life cycle of at least one of the applications 370. The window manager 342 may manage Graphical User Interface (GUI) resources used by a screen. The multimedia manager 343 may recognize a format required for reproduction of various media files, and may perform encoding or decoding of a media file by using a codec suitable for the corresponding format. The resource manager 344 may manage resources of a source code, a memory, and a storage space of at least one of the applications 370.

The power manager 345 may operate together with, for example, a Basic Input/Output System (BIOS) or the like to manage a battery or power source and may provide power information or the like required for the operations of the electronic device. The database manager 346 may generate, search for, and/or change a database to be used by at least one of the applications 370. The package manager 347 may manage installation or an update of an application distributed in a form of a package file.

For example, the connectivity manager 348 may manage wireless connectivity such as Wi-Fi or Bluetooth. The notification manager 349 may display or notify of an event such as an arrival message, promise, proximity notification, and the like in such a way that does not disturb a user. The location manager 350 may manage location information of an electronic device. The graphic manager 351 may manage a graphic effect which will be provided to a user, or a user interface related to the graphic effect. The security manager 352 may provide all security functions required for system security, user authentication, or the like. According to an embodiment of the present disclosure, when the electronic device (e.g., the electronic device 101) has a telephone call function, the middleware 330 may further include a telephony manager for managing a voice call function or a video call function of the electronic device.

The middleware 330 may include a middleware module that forms a combination of various functions of the above-described components. The middleware 330 may provide a module specialized for each type of OS in order to provide a differentiated function. Further, the middleware 330 may dynamically remove some of the existing components or add new components.

The API 360 (e.g., the API 145) is, for example, a set of API programming functions, and may be provided with a different configuration according to an OS. For example, in the case of Android or iOS, one API set may be provided for each platform. In the case of Tizen, two or more API sets may be provided for each platform.

The applications 370 (e.g., the application programs 147) may include, for example, one or more applications which may provide functions such as a home 371, a dialer 372, an SMS/MMS 373, an Instant Message (IM) 374, a browser 375, a camera 376, an alarm 377, contacts 378, a voice dial 379, an email 380, a calendar 381, a media player 382, an album 383, a clock 384, health care (e.g., measuring exercise quantity or glucose), or environment information (e.g., providing atmospheric pressure, humidity, or temperature information).

According to an embodiment of the present disclosure, the applications 370 may include an application (hereinafter, referred to as an "information exchange application" for convenience of description) that supports exchanging information between the electronic device (e.g., the electronic device 101) and an external electronic device (e.g., the electronic device 102 or 104). The information exchange application may include, for example, a notification relay application for transferring specific information to an external electronic device or a device management application for managing an external electronic device.

For example, the notification relay application may include a function of transferring, to the external electronic device (e.g., the electronic device 102 or 104), notification information generated from other applications of the electronic device 101 (e.g., an SMS/MMS application, an e-mail application, a health management application, or an environmental information application). Further, the notification relay application may receive notification information from, for example, an external electronic device and provide the received notification information to a user.

The device management application may manage (e.g., install, delete, or update), for example, at least one function of an external electronic device (e.g., the electronic device 102 or 104) communicating with the electronic device (e.g., a function of turning on/off the external electronic device itself (or some components) or a function of adjusting the brightness (or a resolution) of the display), applications operating in the external electronic device, and services provided by the external electronic device (e.g., a call service or a message service).

According to an embodiment of the present disclosure, the applications 370 may include applications (e.g., a health care application of a mobile medical appliance or the like) designated according to an external electronic device (e.g., attributes of the electronic device 102 or 104). According to an embodiment of the present disclosure, the applications 370 may include an application received from an external electronic device (e.g., the server 106, or the electronic device 102 or 104). According to an embodiment of the present disclosure, the applications 370 may include a preloaded application or a third party application that may be downloaded from a server. The names of the components of the program module 310 of the illustrated embodiment of the present disclosure may change according to the type of operating system.

According to various embodiments, at least a part of the programming module 310 may be implemented in software, firmware, hardware, or a combination of two or more thereof. At least some of the program module 310 may be implemented (e.g., executed) by, for example, the processor. At least some of the program module 310 may include, for example, a module, a program, a routine, a set of instructions, and/or a process for performing one or more functions.

The term "module" as used herein may, for example, mean a unit including one of hardware, software, and firmware or a combination of two or more of them. The "module" may be interchangeably used with, for example, the term "unit", "logic", "logical block", "component", or "circuit". The "module" may be a unit of an integrated component element or a part thereof. The "module" may be a unit for performing one or more functions or a part thereof. The "module" may be mechanically or electronically implemented. For example, the "module" according to the present disclosure may include at least one of an Application-Specific Integrated Circuit (ASIC) chip, a Field-Programmable Gate Arrays (FPGA), and a programmable-logic device for performing operations which has been known or are to be developed hereinafter.

According to various embodiments, at least some of the devices (for example, modules or functions thereof) or the method (for example, operations) according to the present disclosure may be implemented by a command stored in a computer-readable storage medium in a programming module form. The instruction, when executed by a processor (e.g., the processor 120), may cause the one or more processors to execute the function corresponding to the instruction. The computer-readable recoding media may be, for example, the memory 130.

The computer readable recoding medium may include a hard disk, a floppy disk, magnetic media (e.g., a magnetic tape), optical media (e.g., a Compact Disc Read Only Memory (CD-ROM) and a Digital Versatile Disc (DVD)), magneto-optical media (e.g., a floptical disk), a hardware device (e.g., a Read Only Memory (ROM), a Random Access Memory (RAM), a flash memory), and the like. In addition, the program instructions may include high class language codes, which can be executed in a computer by using an interpreter, as well as machine codes made by a compiler. The aforementioned hardware device may be configured to operate as one or more software modules in order to perform the operation of the present disclosure, and vice versa.

Figure 4:
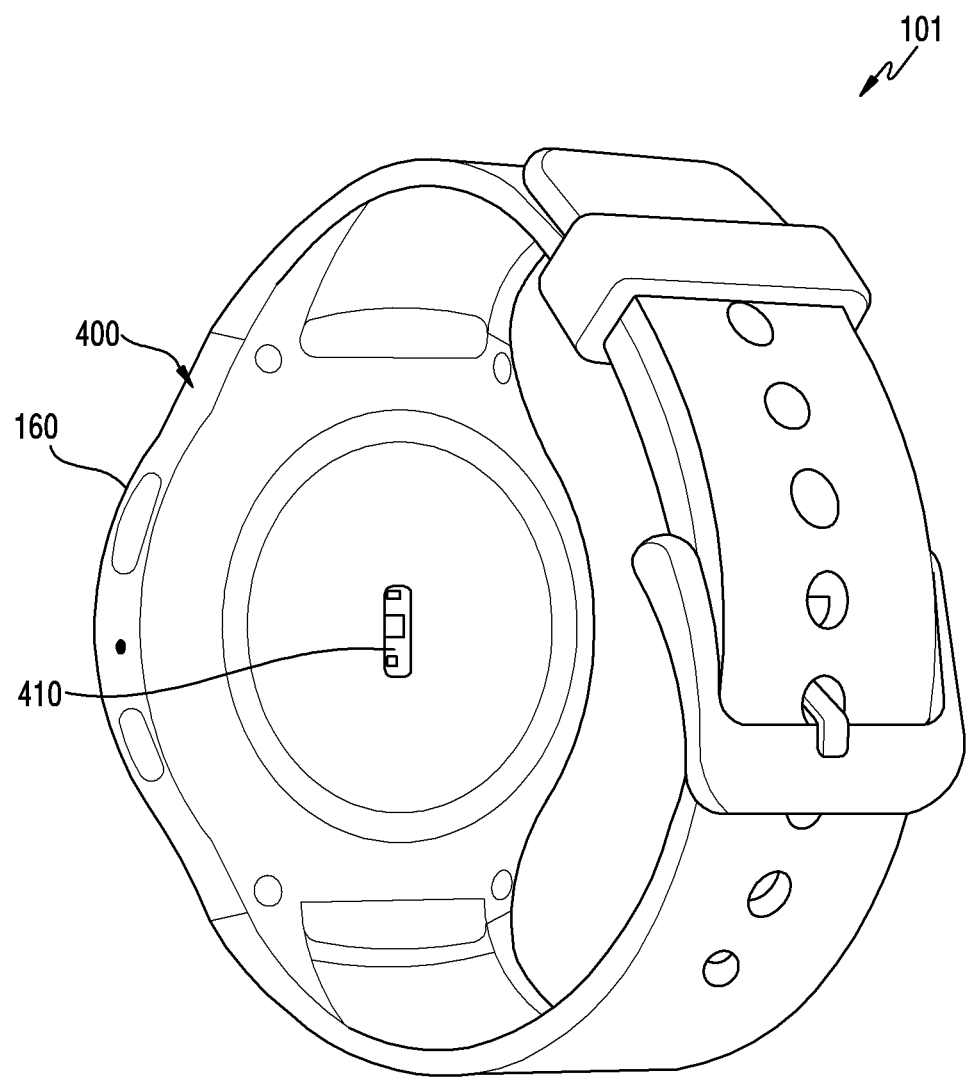
FIG. 4 illustrates a wearable electronic device according to various embodiments.

FIG. 4 illustrates an example of an electronic device according to various embodiments. Such a structure may be implemented in the electronic device 101 of FIG. 1 or the electronic device 201 of FIG. 2.

Referring to FIG. 4, the electronic device 101 may include a housing 400, a display 160, a ppg sensor 410 (e.g., the biometric sensor 240I).

The housing 400 may provide a space for mounting components (e.g., the display 160, the ppg sensor 410, etc.). The housing 400 may be implemented in various forms. In FIG. 4, the housing 400 is implemented in, but not limited to, a circular member attachable to part of a user's body. The housing 400 according to various embodiments may be implemented in another form than the circle, such as an octagon or other polygon. In various embodiments, the housing 400 may be implemented in a rectangle, a square, or an oval attachable to part of the user's body.

The display 160 may be used to provide information processed at the electronic device 101. In various embodiments, the display 160 may display a screen or a user interface displaying information processed at the electronic device 101. In various embodiments, the display 160 may be disposed on a front side of the housing 400, to provide the information processed at the electronic device 101. In various embodiments, the display 160 may be exposed through part of the front side of the housing 400, to provide the information processed at the electronic device 101.

The ppg sensor 410 may be used to measure a heart rate of the user (or the user related to the electronic device 101) of the electronic device 101. The ppg sensor may also measure glucose or blood pressure of the user. In various embodiments, the ppg sensor 410 may emit light toward part of the user body which contacts the electronic device 101, using one or more light emitting diodes or lasers of the ppg sensor 410. The ppg sensor 410 may receive a reflected light of the emitted light, using one or more photodiodes or other light detectors of the ppg sensor 410. The ppg sensor 410 may convert information of the reflected light to an electric signal. The electric signal obtained at the ppg sensor 410 may be forwarded to the processor 120 of the electronic device 101. The forwarded electric signal may include the user heart rate information.

To measure the user's heart rate or other biometric information such as glucose, the ppg sensor 410 may be disposed in a rear side or the front side of the housing 400. In various embodiments, to measure the user's heart rate or other biometric information such as glucose, the ppg sensor 410 may be exposed through part of the rear side or the front side of the housing 400. The rear side may be disposed on the opposite side of the front side. The rear side or the front side may be configured to make non-invasive contact part of the user body. The ppg sensor 410, which is exposed through part of the rear side or the front side of the housing 400 to contact part of the user body, may measure the user's heart rate or other biometric information such as glucose.

Although not depicted in FIG. 4, the electronic device 101 may further include a film which is attached to, disposed on (over), superimposed on (over), or overlaid on (over) the ppg sensor 410. The film may be used to measure glucose levels, and may include chemochromic materials (materials which respond to the exposure of different chemicals with a change in color). The film used to measure the glucose levels may be configured with a translucent state or a transparent state, to apply the light of a required wavelength to the user. The ppg sensor 410 may further include an element (e.g., a light emitting diode) for emitting the light of the required wavelength.

Figure 5:
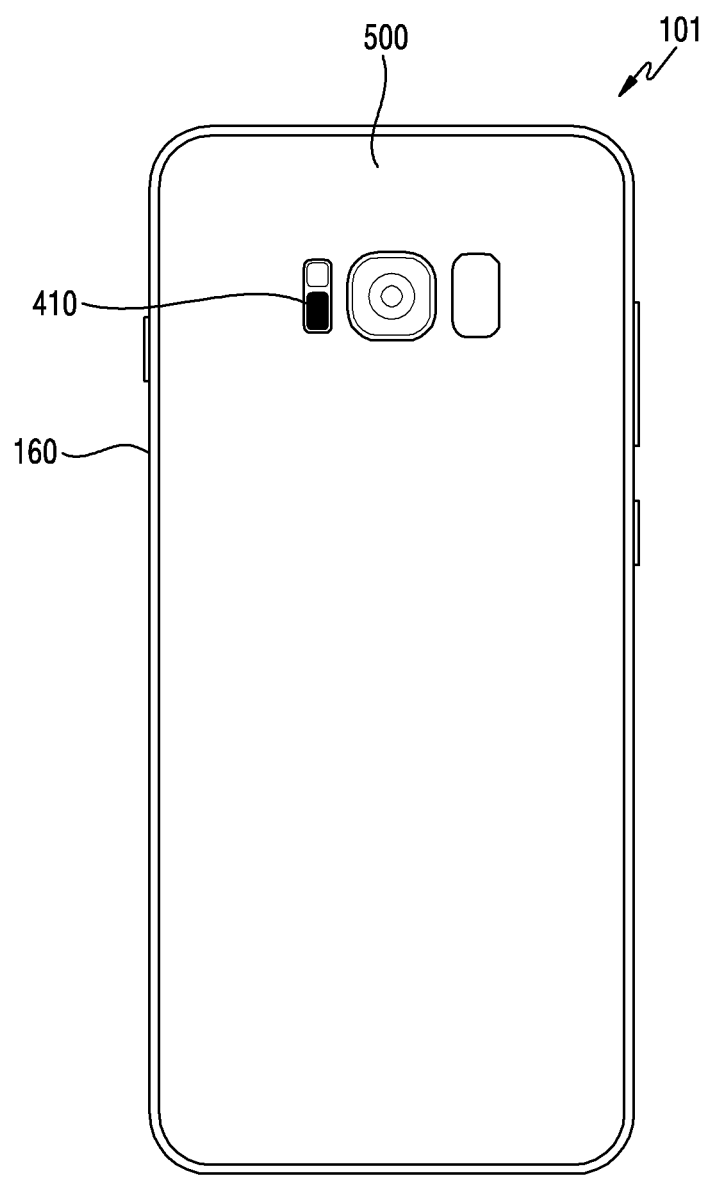
FIG. 5 illustrates a smartphone according to various embodiments.

Whereas FIG. 4 illustrated a wearable electronic device, FIG. 5 illustrates another example of a smartphone according to various embodiments. Such a structure may be implemented in the electronic device 101 of FIG. 1 or the electronic device 201 of FIG. 2.

Referring to FIG. 5, the electronic device 101 may include a housing 500, a display 160, and a ppg sensor 410 (e.g., the biometric sensor 240I).

The housing 500 may provide a space for mounting components (e.g., the display 160, the ppg sensor 410, etc.). The housing 500 may be implemented in various forms. In FIG. 5, the housing 500 is implemented in a rectangle having a curve for user's grip to ease the understanding. The housing 500 according to various embodiments may be implemented in various forms, wherein the user grips the electronic device 101.

The display 160 may be used to provide information processed at the electronic device 101. In various embodiments, the display 160 may display a screen or a user interface of the information processed at the electronic device 101. In various embodiments, the display 160 may be disposed on a front side of the housing 500, to provide the information processed by the electronic device 101. In various embodiments, the display 160 may be exposed through part of the front side of the housing 500, to provide the information processed at the electronic device 101.

The ppg sensor 410 may be used to measure the heart rate or other biometric information such as glucose of the user of the electronic device 101. To measure the user's heart rate or other biometric information of the electronic device 101, the ppg sensor 410 may be exposed in the rear side or the front side of the housing 500. In various embodiments, the ppg sensor 410 may be exposed through part of the rear side or the front side of the housing 500, to measure the user's heart rate of the electronic device 101.

The ppg sensor 410 may be disposed in an upper portion of the rear side of the housing 500, wherein the user gripping the electronic device 101 (or the housing 500) may contact the ppg sensor 410 with his/her body part (e.g., a finger). However, the position of the ppg sensor 410 is not limited to this. The ppg sensor 410 may be disposed at various positions, so as to contact the ppg sensor 410 with the user's body part.

Although not depicted in FIG. 5, the electronic device 101 may further include a film which is attached to, disposed on (over), superimposed on (over), or overlaid on (over) the ppg sensor 410. The film may be used to measure the glucose levels, and may include the chemochromic materials. The film used to measure the glucose level may be configured with a translucent state or a transparent state, to apply light of a specific wavelength to the user. If the film is transparent, the ppg sensor 410 may further include an element (e.g., a light emitting diode) for emitting the light of the required wavelength.

Figure 6:
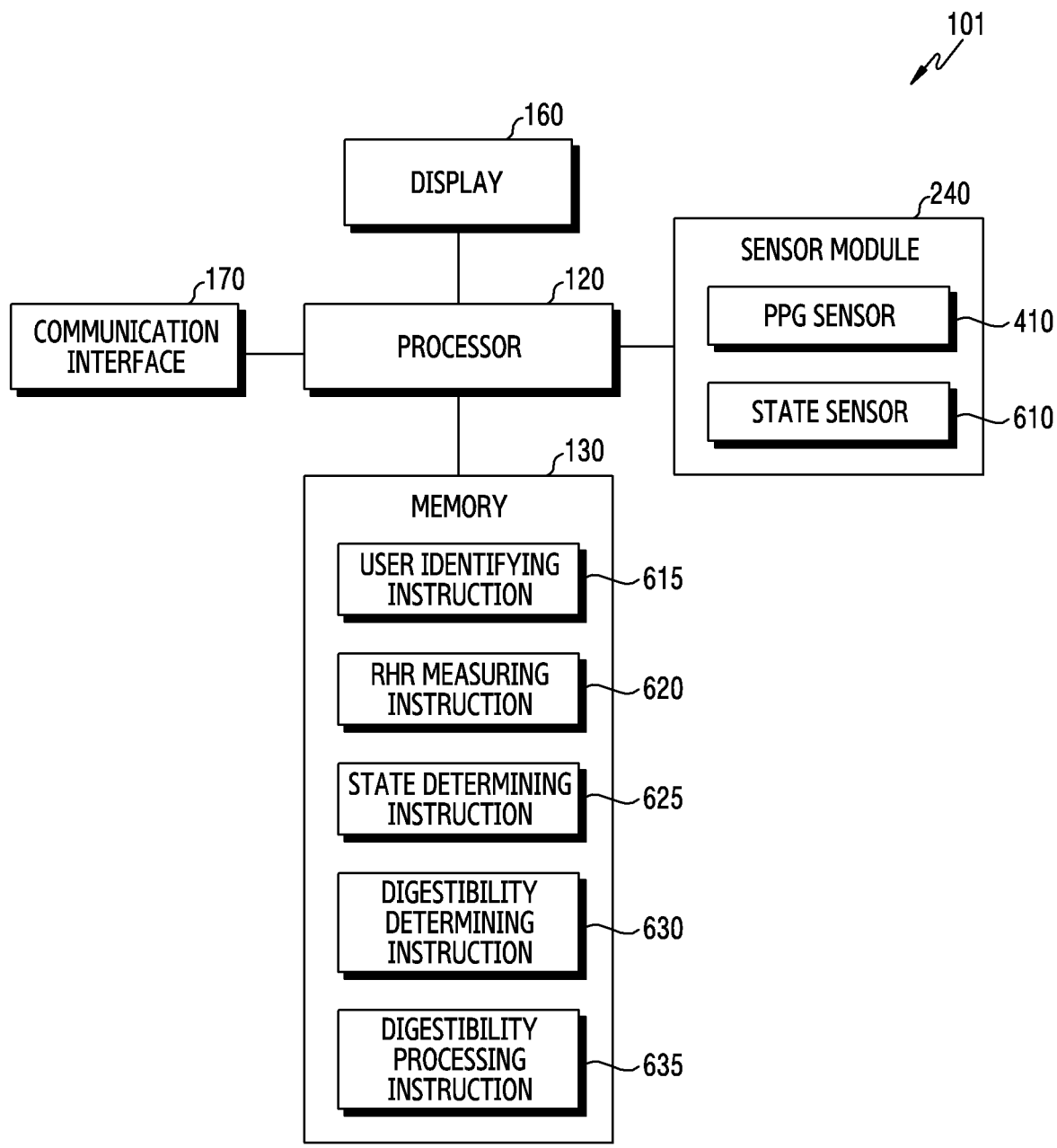
FIG. 6 illustrates a block diagram of an electronic device according to various embodiments.

FIG. 6 illustrates a block diagram of an electronic device according to various embodiments. Such a configuration may be included in the electronic device 101 of FIG. 1 or the electronic device 201 of FIG. 2.

Referring to FIG. 6, the electronic device 101 may include one or more of a processor 120, a memory 130, a display 160, a communication interface 170, or a sensor module 240.

The processor 120 may control operations of the electronic device 101. In various embodiments, to obtain information about a user's resting heart rate, the processor 120 may control one or more of the memory 130, the display 160, the communication interface 170, or the sensor module 240.

Herein, the resting heart rate may refer to user's heart beats per unit time in a generally sedentary state, but permitting varying states of food consumption including, but not limited to, fasting (empty stomach), consuming food, and various states after food consumption. In various embodiments, the resting heart rate may refer to a heart rate measured before sleeping and wakeup. In various embodiments, the resting heart rate may refer to a heart rate measured when the user does not move (or movements are considered medically non-strenuous) over five minutes or moves slightly. The resting heart rate may be a parameter indicating aerobic ability of the user body.

In various embodiments, the processor 120 may control one or more of the memory 130, the display 160, the communication interface 170, or the sensor module 240, to determine user's food intake. In various embodiments, the processor 120 may control one or more of the memory 130, the display 160, the communication interface 170, or the sensor module 240, to identify or monitor a change (or a difference) of the resting heart rate from the obtained resting heart rate information. In various embodiments, the processor 120 may control one or more of the memory 130, the display 160, the communication interface 170, or the sensor module 240, to obtain a digestibility or an Energy Intake Rate Index (EIRI) of the food taken by the user based on the change of the resting heart rate. The digestibility (or EIRI) may be a parameter indicating a relationship between an amount of food consumed by the user and the food digestion time. In various embodiments, the digestibility may indicate a rate at which a specific food taken by the user is digested. In various embodiments, the processor 120 may control one or more of the memory 130, the display 160, the communication interface 170, or the sensor module 240, to process the digestibility information.

It is noted that food consumption generally results in gradual drop in resting heart rate (RHR) where the resting heart rate begins to drop shortly after food consumption. The RHR continues to drop to bottom value, before starting to rise again. In certain embodiments, the digestibility of the food can be the difference in RHR from peak to bottom divided by the time of the peak to bottom.

The processor 120 may be configured to execute various operations. In various embodiments, the processor 120 may operate with normal power supplied (e.g., with power over reference power). In various embodiments, the processor 120 may operate in a normal power mode or an activate mode (or an active mode) where the normal power is supplied from the electronic device 101. In various embodiments, the processor 120 may operate with no normal power supplied (e.g., with the power below the reference power) or with restricted capability to reduce power consumption. In various embodiments, the processor 120 may operate in a low power mode, an idle mode, a sleep mode, or a deactivated mode (or a de-active mode). If the processor 120 includes a plurality of processors, the processor 120 may include an auxiliary processor for controlling the sensor module 240. In various embodiments, the auxiliary processor may be a sensor hub. The sensor hub of the processor 120 may normally operate in the low power state. In various embodiments, even if at least some of the processors of the processor 120 operate in the low power mode (the idle mode, the sleep mode, or the deactivate mode), the sensor hub of the processor 120 may operate in the normal mode or in the activate mode.

In various embodiments, the processor 120 may control the sensor module 240 to obtain user biometric information. The user biometric information may refer to a state of the user body. In various embodiments, the user biometric information may include user movement state information, user heart rate information, and user glucose level information. The obtained user biometric information may be stored in the memory 130 or temporarily stored.

In various embodiments, the processor 120 may control a state sensor 610 (e.g., the gyro sensor 240B, the acceleration sensor 240E, the grip sensor 240F, etc.). In various embodiments, to measure the resting heart rate, the processor 120 may determine or identify whether the user is in a sedentary or resting state. The processor 120 may determine or identify whether the user is in the sedentary or resting state, by analyzing the received, acquired, or obtained information through the state sensor 610. The received, acquired, or obtained information through the state sensor 610 may include information indicating a user is moving in a manner that would be considered medically strenuous. In various embodiments, the received, acquired, or obtained information through the state sensor 610 may include information indicating whether the user grips or wears the electronic device 101, information indicating whether the user is stationary/sedentary, and information indicating whether the user remains stationary/sedentary. In various embodiments, the received, acquired, or obtained information through the state sensor 610 may include information, if the user moves, about a movement type and a movement time.

In various embodiments, the processor 120 may control the ppg sensor 410. The processor 120 may measure the resting heart rate using the ppg sensor 410, based on determining or identify the stable, stationary, sedentary, or resting state of the user. In various embodiments, in the information received or obtained through the ppg sensor 410 of the activate state (e.g., the activate mode), the processor 120 may determine information corresponding to a time or a timing where the user is resting, as the resting heart rate information. Herein, the activate state may supply the normal power to the ppg sensor 410. The ppg sensor 410 operating in the activate state may obtain user's heart rate information from part of the user body. In various embodiments, in response to determining or identifying the resting user, the processor 120 may switch the ppg sensor 410 of the deactivate state (e.g., the de-active mode) to the activate state. Herein, the deactivate state might not supply the normal power to the ppg sensor 410. The deactivated state may be configured to reduce power consumption of the electronic device 101. The processor 120 may obtain the resting heart rate information, based on the information received or obtained through the ppg sensor 410 of the activate state.

Although not depicted in FIG. 6, in yet another embodiment, the processor 120 may measure the glucose level. Using the configuration (e.g., the film) for measuring the glucose level, the processor 120 obtain sugar amount and sugar digestion information in the food taken by the user. The sugar amount can include grams of sugar. The sugar digestion information can include, for example, the hypoglycemic index.

In FIG. 6, the electronic device 101 obtains the biometric information through the sensor module 240. The electronic device 101 may obtain the biometric information from another electronic device such as the external electronic device 102. In various embodiments, the electronic device 101 may receive the biometric information from the external electronic device 102 including a sensor module, through the communication interface 170.

In various embodiments, the processor 120 may determine that the user consumes food, using the information obtained through the sensor module 240. In various embodiments, the processor 120 may identify that the user's resting heart rate increases, based on the information obtained through the sensor module 240. The processor 120 may determine the user's food consumption, based on the increase of the user's resting heart rate. In various embodiments, when the electronic device 101 includes the configuration for measuring the sugar, the processor 120 may identify a change trend or a level of the user's sugar, from the information obtained through the sensor module 240. The processor 120 may determine the user's food intake, based at least in part on the identified sugar change trend or sugar level.

In various embodiments, the processor 120 may determine the user's food intake using information received through the communication interface 170. In various embodiments, the processor 120 may transmit and receive food related messages to and from the external electronic device 102 or the server 106 using the communication interface 170. The food related message may include information of the food consumed by the user. Food related messages may be detected by including various keywords, such as food types, food attributes (calories), etc.

In various embodiments, the food information may include payment information of the food taken by the user, place information of the user's food intake, information occurred by a particular application predetermined to be food related, such as Lose It!, MyFitnessPal, Fooducate, Diet Watchers Diary, and so on.

The payment information of the food taken by the user may include data for identifying the food taken by the user.

The payment information of the food taken by the user may be received from a server which provides a payment service. The payment service server may include a mobile payment service server such as Samsung Pay, a server of a bank or a financial company which issues a credit card or an electronic card, or a server of a bank or a financial company which purchases a slip of a card transaction made at a store.

The place information of the user's food intake may include information for identifying a place where the user takes the food, such as a GPS reading, entity where a charge for food is made, etc.

The place information of the user's food intake may include point of interest (POI) information. The POI information may include place data corresponding to a location of the electronic device 101. In various embodiments, the POI information may include current area or place (e.g., a store, an institution, a facility, a building, etc.) information of the electronic device 101. In various embodiments, the POI information may include business name data of the store where the electronic device 101 is located. The data included in the place information of the user's food intake is not limited to those.

The place information of the user's food intake may include sensing information. The sensing information may include data sensed at the place of the electronic device 101. In various embodiments, the sensing information may include data sensed using one or more of the communication interface 170 or the sensor module 240 at the place of the electronic device 101. In various embodiments, the sensing information may include data collected using one or more a cellular radio signal (for example the radio tower location), a Wi-Fi signal (location of the Wi-Fi network), a Bluetooth signal (using the location of the paired device), an NFC signal (using location information of the point of sale), or other radio signal, received at the place of the electronic device 101. In various embodiments, the sensing information may include data contained in a signal received from a device (e.g., a Wi-Fi communication access point (AP), a beacon, etc.) at the place of the electronic device 101, a device (e.g., a base station) near the electronic device 101, or a GPS satellite. The data included in the sensing information is not limited to those.

The place information of the user's food intake may be received from a POI server, a big data server, a mobile service provider server, a beacon server, and the like.

The information occurred by the food related application may be transmitted or received through a food delivery service application stored in the electronic device 101, such as Grubhub or ChowNow. In various embodiments, the information occurred by the food related application may be information for ordering a particular food. In various embodiments, the information occurred by the food related application may be information indicating delivery complete of the particular food.

In various embodiments, the processor 120 may identify the change of the resting heart rate, from the heart rate information. In response to determining the user's food intake, the processor 120 identify the change of the resting heart rate based on the heart rate information. To determine the digestibility, the processor 120 may identify the change of the resting heart rate from the resting heart rate information stored in the memory 130 or temporarily stored. Upon identifying the change of the resting heart rate, the processor 120 may identify required data for determining the digestibility, from the resting heart rate information. In various embodiments, the required data for determining the digestibility may include one or more of a first time at which the resting heart rate decreases, a second time at which the resting heart rate changes from increases or reaches the same resting heart rate as previously measured on an empty stomach, or the resting heart rate values of the first time and the second time. Determining the digestibility shall be described in more detail in FIG. 7 and FIG. 8.

In various embodiments, the processor 120 may process the digestibility information.

In various embodiments, the processor 120 may store or temporarily store the digestibility information. In various embodiments, the processor 120 may map the food taken by the user with the digestibility information in a data portion of memory 130. The processor 120 may store the digestibility information mapped to the food taken by the user. In various embodiments, the processor 120 may map a user identified using user authentication (e.g., unlocking using facial recognition, unlocking using iris scan, unlocking using speech recognition, unlocking using fingerprint, unlocking using pattern, unlocking using password, etc.), with the digestibility information. The processor 120 may store the digestibility information mapped to the identified user.

In various embodiments, the processor 120 may provide digestibility related information using the stored digestibility information. In various embodiments, the digestibility related information may include data of an estimated digestion time of the food taken by the user. In various embodiments, the digestibility related information may include data indicating a recommended mealtime. In various embodiments, the digestibility related information may include notification or alarm data for glucose check. In various embodiments, the digestibility related information may include food advertising information. In various embodiments, the digestibility related information may include data indicating a recommended menu or a menu at a special price. In various embodiments, the digestibility related information may include data indicating a relationship between the user's food intake time and a sleeping quality.

In various embodiments, the processor 120 may display the digestibility information on the display 160.

In various embodiments, using the communication interface 170, the processor 120 may transmit one or more of the digestibility information or the digestibility related information to other electronic device such as the external electronic device 102 or the server 106. The transmitted digestibility information and the transmitted digestibility related information may be displayed at the other electronic device.

The memory 130 may execute instructions stored in the memory 130, based on signaling with the processor 120.

In various embodiments, the memory 130 may include user identifying instructions 615 for identifying the user from user information. In various embodiments, the user information may include fingerprint information, iris scan information, speech recognition information, facial recognition information, pattern information, and password information. The user identifying instructions 615 may be used to identify who is using the electronic device 101, or whether the user of the electronic device 101 is legitimate, based on the user information.

In various embodiments, the memory 130 may include resting heart rate (RHR) measuring instructions 620 for controlling the ppg sensor 410. In various embodiments, the RHR measuring instruction 620 may be used to identify RHR information in the information obtained through the ppg sensor 410. In various embodiments, the RHR measuring instructions 620 may be used to activate the deactivated ppg sensor 410, in response to determining that the user of the electronic device 101 is at rest.

In various embodiments, the memory 130 may include state determining instructions 625 for controlling the state sensor 610. In various embodiments, the state determining instructions 625 may be used to determine or identify whether the user is at rest (e.g., whether the RHR is measurable).

In various embodiments, the memory 130 may include digestibility determining instructions 630. In various embodiments, the digestibility determining instructions 630 may be used to determine or identify the digestibility of the food taken by the user, based on the data obtained from the sensor module 240.

In various embodiments, the memory 130 may include digestibility processing instructions 635. In various embodiments, the digestibility processing instructions 635 may be used to store or display the digestibility related information. In various embodiments, the digestibility processing instructions 635 may be used to obtain the digestibility related information from the digestibility information. In various embodiments, the digestibility processing instructions 635 may be used to provide one or more of the digestibility information or the digestibility related information to other electronic device.

The communication interface 170 may be used for communications between the external electronic device (e.g., the electronic device 102, the electronic device 104, or the server 106 of FIG. 1) and the electronic device 101.

The sensor module 240 may be used to obtain environment information of the user of the electronic device 101, or the electronic device 101. The sensor module 240 may include the ppg sensor 410 and the state sensor 610.

The ppg sensor 410 may be used to measure the user's heart rate. In various embodiments, the ppg sensor 410 may include one or more of an ECG sensor, a photoplethysmography (PPG) sensor, or a ballistocardiogram (BCG) sensor.

The state sensor 610 may be used to determine the user's state. In various embodiments, the state sensor 610 may include the gesture sensor 240A, the image sensor (e.g., the camera module 291), the gyro sensor 240B, the acceleration sensor 240E, the grip sensor 240F, the proximity sensor 240G, and so on.

In FIG. 6, the electronic device 101 includes the display 160 as the output device, to facilitate the explanations. The electronic device 101 according to various embodiments may further include an output device such as the audio module 280, the indicator 297, the motor 298, or a display of the external electronic device (e.g., the electronic device 102 or 104).

As such, the electronic device 101 according to various embodiments may obtain the user biometric information, obtain the user food intake information, and thus determine the digestibility of the food eaten. The electronic device 101 may provide various information for user's health, by providing the determined digestibility information.

As stated above, a wearable device (e.g., the electronic device 101) according to various embodiments may include a biometric sensor (e.g., the biometric sensor 240I), an output device (e.g., the display 160), and a processor (e.g., the processor 120) operatively coupled with the biometric sensor and the output device, wherein the processor may be configured to obtain food intake information of a user corresponding to the wearable device, to obtain biometric information of the user by using the biometric sensor, to identify a digestibility of the food of the user, based at least in part on a change of the biometric information corresponding to the food intake information, and to provide information of the digestibility, using the output device.

In various embodiments, the digestibility information may include time of the food intake. The time may be determined based at least in part on a timing at which a quantity of the biometric information decreases and a time at which a quantity of biometric information changes increases or the quantity of the biometric information reaches a quantity measured on an empty stomach, or determined based on one or more of food payment information received from an external electronic device or information occurred by a particular application previously determined to be relating to the food.

In various embodiments, the biometric information may include heart rate information of the user.

In various embodiments, the processor may be configured to provide, based at least in part on the digestibility, sleeping information of the user as at least portion of the digestibility information.

According to various embodiments, a wearable device (e.g., the electronic device 101) may include a housing, a display (e.g., the display 160) disposed in a first area of the housing (e.g., the housing 400), one or more sensors (e.g., the ppg sensor 410) electrically connected to one or more terminals contactable to part of a user body through a second area of the housing, a memory (e.g., the memory 130) storing instructions, and one or more processors (e.g., the processor 120) operably coupled with the memory, the one or more sensors, and the display, wherein the one or more processors are configured to execute the stored instructions, and wherein execution of the instructions by the one or more processor causes the one or more processor to perform operations comprising: obtaining resting heart rate information of the user through the one or more sensor, determining user food intake, based at least in part on the obtained resting heart rate information, identifying, in response to the determination, a change of the resting heart rate from the obtained resting heart rate information, determining a digestibility of the food taken by the user, based on the change of the resting heart rate, and storing the digestibility information in the memory.

In various embodiments, the operations further comprise identifying, from the resting heart rate information, a first time at which the resting heart rate decreases and a second time at which the resting heart rate increases or reaches a resting heart rate measured on an empty stomach, and determining the digestibility, based on the first time and the second time.

In various embodiments, the operations further comprise identifying, from the resting heart rate information, a first time at which the resting heart rate decreases and a second time at which the resting heart rate increases or reaches a resting heart rate measured on an empty stomach, and determining the digestibility, based on the first time and the second time.

In various embodiments, the wearable device may further include a communication interface, wherein the operations further comprise transmitting the digestibility information to an electronic device associated with the wearable device through the communication interface.

In various embodiments, the operations further comprises receiving food information from the electronic device associated with the wearable device, and to determining the user food intake, based on the food information and the obtained information.

In various embodiments, wherein the one or more sensors comprise one or more first sensors configured to obtain movement information of the user, and one or more second sensors configured to obtain the heart rate information of the user, wherein the operations further comprise obtaining, in response to identifying that an amount of user movement obtained through the one or more first sensors falls within a designated range, the resting heart rate information through the one or more second sensors. In various embodiments, the one or more first sensors may include one or more of an image sensor, a proximity sensor, a gyro sensor, or an acceleration sensor, and the one or more second sensors may include one or more of an ECG sensor, a PPG sensor, or a BCG sensor.

In various embodiments, the one or more sensors may include one or more first sensors configured to obtain movement information of the user, and one or more second sensors configured to obtain heart rate information of the user, wherein the one or more processors may be configured to execute the stored instructions to switch, in response to identifying that a change of the user movement obtained through the one or more first sensors falls within a designated range, an operation state of the one or more second sensors from an idle state to an active state.

In various embodiments, the one or more sensors may include a PPG sensor and a film disposed over the PPG sensor.

In various embodiments, the wearable device may further include a communication interface, wherein the operations further comprise obtaining the digestibility information corresponding to the food through the communication interface, storing the digestibility information in the memory, receiving information indicating the user food intake, from an external electronic device, and in response to identifying the user food intake corresponding to the stored digestibility information from the received information, determining an estimated digestion time of the food, based on the stored digestibility information. In various embodiments, the operations may include displaying information of the determined estimated digestion time in the form of a progress bar. In various embodiments, the operations may include transmitting the determined estimated digestion time information to the external electronic device.

According to various embodiments, an electronic device (e.g., electronic device 101) may include a communication interface (e.g., the communication interface 170), an output device (e.g., the display 160), and one or more processors (e.g., the processor 120) operably coupled with the communication interface and the output device and configured to obtain information of food taken by a user of the electronic device, to obtain a resting heart rate of the user from a wearable device associated with the electronic device, determine digestibility of the food based at least in part on the food information and the resting heart rate information, and to provide digestibility information.

In various embodiments, the one or more processors may be configured to transmit a signal for providing the digestibility information to the wearable device.

In various embodiments, the one or more processors may be configured to provide, based at least in part on the digestibility, user sleeping information as at least a portion of the digestibility information.

Figure 7:
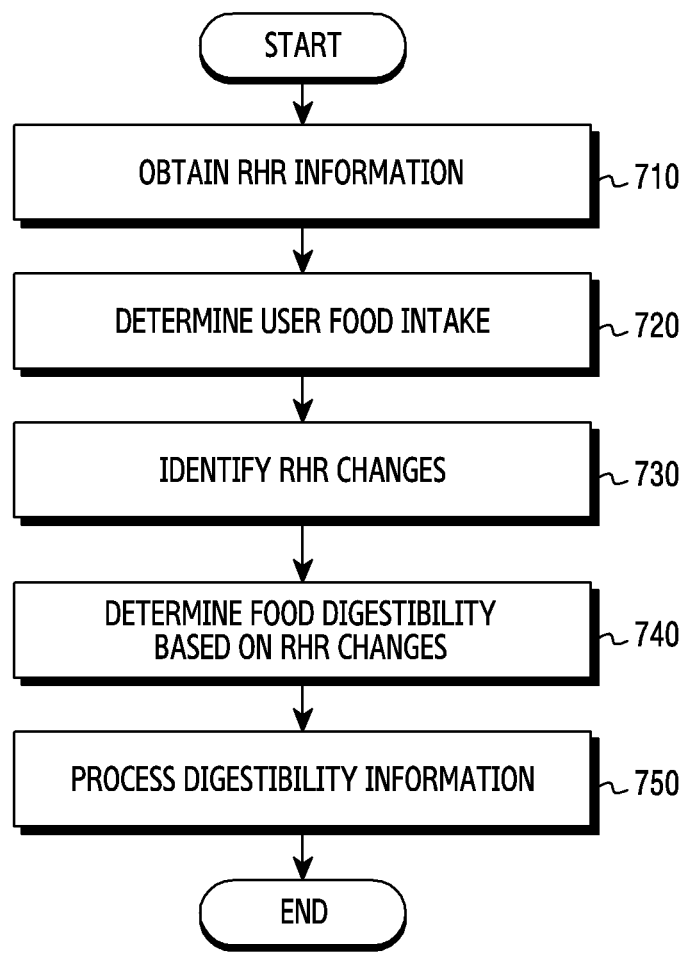
FIG. 7 illustrates an example of operations of an electronic device according to various embodiments.
Figure 8:
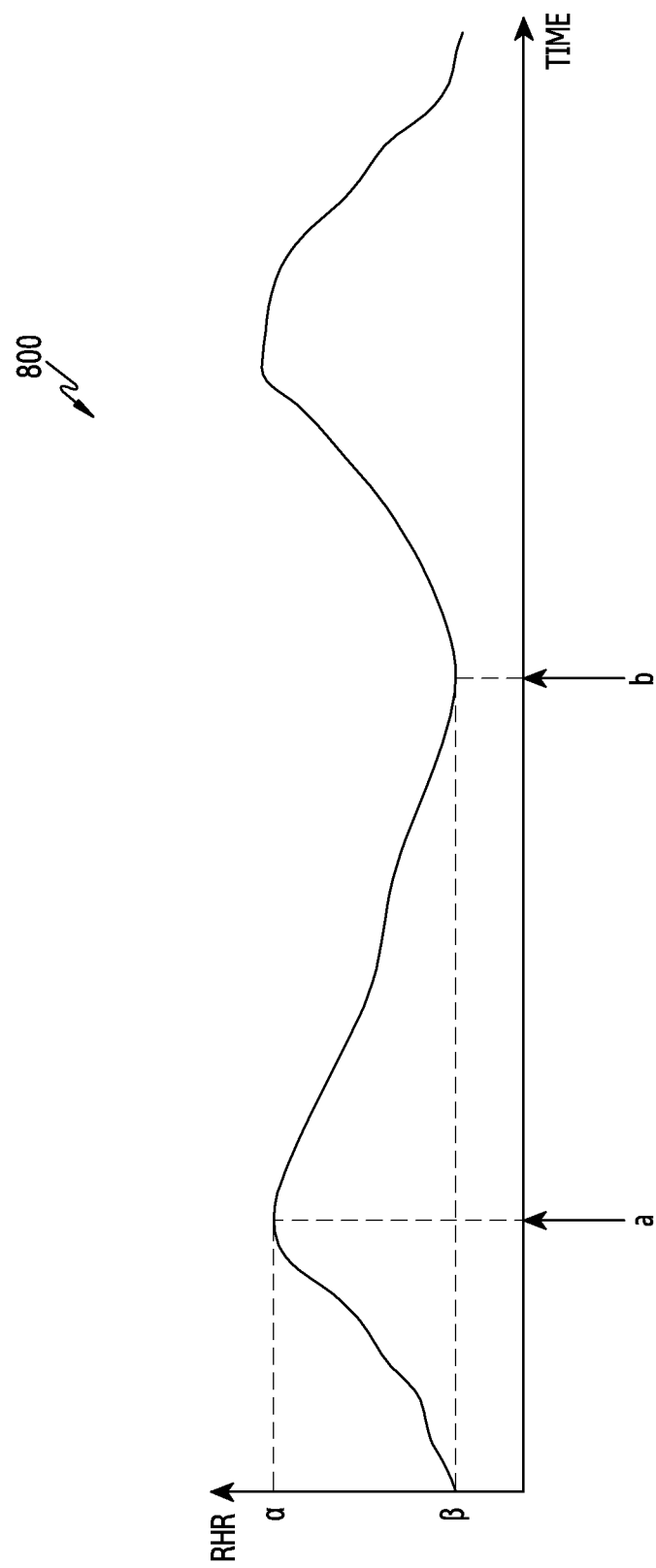
FIG. 8 illustrates a graph showing changes of a resting heart rate.

FIG. 7 illustrates an example of operations of an electronic device according to various embodiments. FIG. 8 illustrates a graph showing (Resting Heart Rate) RHR changes. The operations of FIG. 7 may be carried out by the electronic device 101 of FIG. 1, the electronic device 201 of FIG. 2, the electronic device 101 of FIG. 6, the component (e.g., the processor 120) of the electronic device 101, or the component (e.g., the processor 210) of the electronic device 201.

Referring to FIG. 7, in operation 710, the processor 120 may obtain RHR information. In various embodiments, the processor 120 may be configured to obtain the RHR information using the RHR measuring instructions 620. The RHR may indicate the heart rate of the user who is resting, per unit time (e.g., heart beats/minute). In various embodiments, the RHR may indicate the heart rate measured before sleeping or wakeup. In various embodiments, the RHR may indicate the heart rate measured when the user does not move more than five minutes or moves slightly.

In various embodiments, the processor 120 may obtain user movement information using the state sensor 610. In some embodiments, RHR may be a known quantity that is stored in memory after usage over a period of time.

Based on the obtained user movement information, the processor 120 may determine whether the user is at rest. In various embodiments, the processor 120 may determine that a user movement degree falls below a reference value, based on the obtained user movement information. Herein, the reference value may be a parameter for determining whether the user movement degree corresponds to the resting state. In various embodiments, the reference value may be fixed. In various embodiments, the reference value may adaptively change. In some embodiments, the reference value may be higher for individuals who are very active. On the other hand, the reference value may be lower for individuals who are not normally very active. For example, climbing a flight of stairs may be a resting state for a person that is young and in good physical health, but may be a state of exertion for an elderly person, with arthritis. The reference value may change based on machine learning, or according to configuration of an input. The reference value may be configured independently per user.

Based on determining that the user movement degree below the reference value, the processor 120 may obtain RHR information. In various embodiments, if receiving the user's heart rate information through the ppg sensor 410 (e.g., if the heart rate 410 is active), the processor 120 may obtain data corresponding to a time interval where the user movement degree falls below the reference value, from data of the user heart rate information. The processor 120 may determine the obtained data as the RHR information. It is noted that the ppg sensor 410 can consume considerable power and might not be needed to measure the user's heart rate at all times. Therefore, the ppg sensor 410 might be kept in a deactivated state until needed. In various embodiments, if the ppg sensor 410 is deactivated, the processor 120 may switch the ppg sensor 410 from the deactivate state to the activate state, in response to determining the user movement degree below the reference value. The processor 120 may acquire the RHR information using the activated ppg sensor 410.

In various embodiments, the processor 120 may store or temporarily store the acquired RHR information.

Figure 9A:
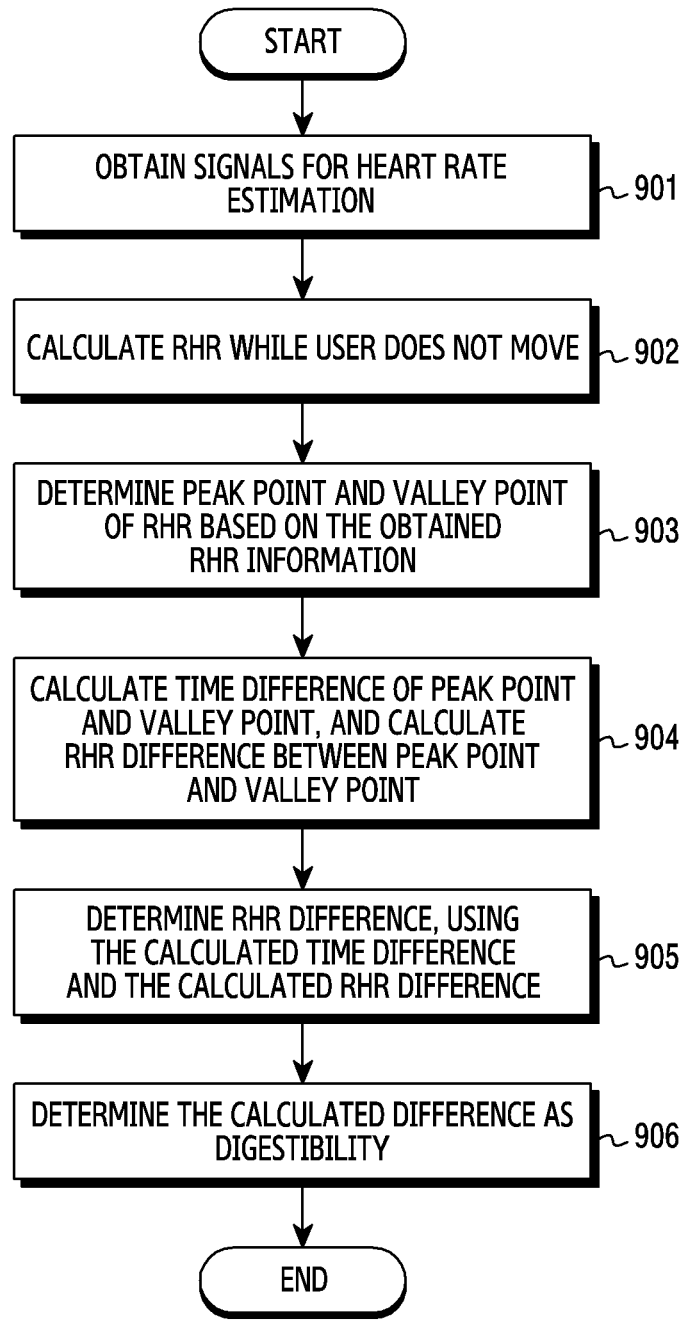
FIG. 9A illustrates an example of operations of an electronic device for determining a digestibility according to various embodiments.
Figure 9B:
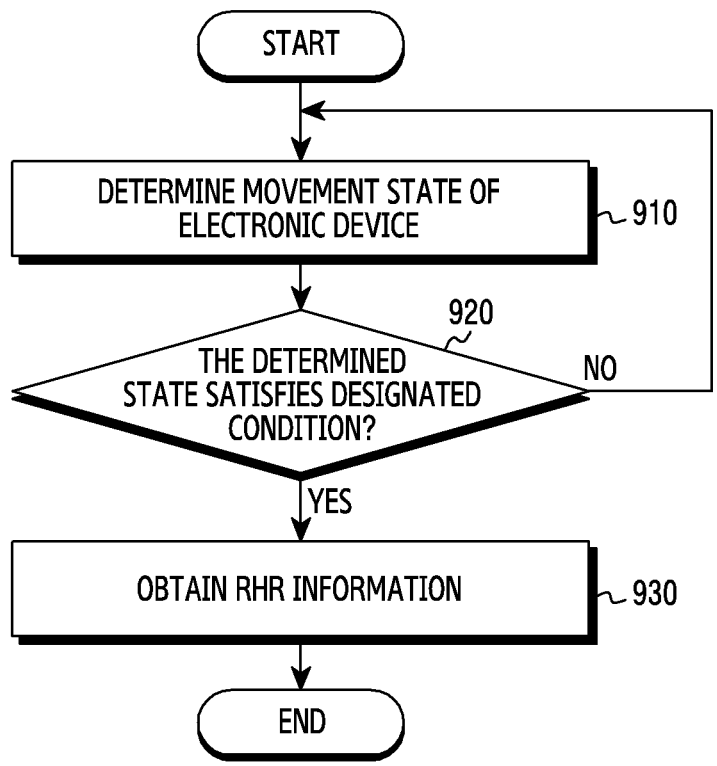
FIG. 9B illustrates an example of operations of an electronic device for obtaining resting heart rate information according to various embodiments.

Acquiring the RHR information shall be described in further detail in FIG. 9B.

In operation 720, the processor 120 may determine the user's food intake. The processor 120 may determine the user's food intake, using the RHR measuring instruction 620 stored in the memory 130. In various embodiments, the processor 120 may determine the user's food intake, based at least in part on a user input, the obtained RHR information, and food information received through the communication interface 170. For example, during the food intake, the RHR might start rising. Detection of the RHR rising can result in a determination of user food intake.

In various embodiments, the processor 120 may determine the user's food intake, based on the user input. In various embodiments, the processor 120 may control the display 160 to display a user interface (UI) including a region for receiving the input. The processor 120 may receive an input on the region of the displayed UI. The region may include one or more of an object (e.g., an icon) for determining whether the user takes a food, an object (e.g., a character input window, a menu select, etc.) for determining a type of the food taken by the user, or an object (e.g., a character input window, a menu select, etc.) for determining a place where the user takes the food. Based on the input received in the region, the processor 120 may determine the user's food intake.

In various embodiments, the processor 120 may identify whether the user's RHR increases, by comparing the obtained RHR information to prior obtained RHR information. The processor 120 may determine that the user is consuming food finishes the food, based on detection of the user's RHR increase. In various embodiments, referring to FIG. 8, a graph 800 may show RHR changes. A horizontal axis of the graph 800 may indicates the time, and a vertical axis of the graph 800 may indicate the RHR. The processor 120 may identify that the user's RHR increases in a time interval before a timing a on the horizontal axis of the graph 800, based on the obtained RHR information. Based on identifying the user's RHR increase, the processor 120 may determine that the user is consuming or finishes the food intake.

In various embodiments, the processor 120 may determine the user's food intake, based on the food information. The food information may include payment information of the food taken by the user, place information of the user's food intake, information occurred by a food related application, and so on.

In various embodiments, the processor 120 may receive the payment information of the food taken by the user. The payment information may include information about an item the user paid for. In various embodiments, if the user takes a food and pays $12.00 for the food at a restaurant identified as "00", the processor 120 may obtain information of the payment location (e.g., the 00 restaurant) and the payment amount (e.g., $12.00) from the payment information received from a payment service server through the communication interface 170. Based on the obtained information, the processor 120 may determine the user's food intake.

For example, the processor 120 can use the communication interface 170 to determine the place, e.g., restaurant, that the user is at by identification of the Wi-Fi network. The Wi-Fi network name may include an identification of the restaurant. The food information can be derived from past orders that the user has made at the identified restaurant, popular menu items, or information of the food from the charges that are made using, for example, Samsung Pay or Google Pay.

In various embodiments, the processor 120 may determine the user's food intake by monitoring information transmitted or received through a food related application (e.g., a food delivery service application) of the electronic device 101. In various embodiments, if the user orders a food identified as "YY" from a restaurant identified as "XX" using the food delivery service application, the processor 120 may determine the user's food intake by monitoring a message which orders the YY food of the XX restaurant, transmitted to a server through the food delivery service application, such as GrubHub™. In various embodiments, the processor 120 may determine the user's food intake by monitoring a message indicating delivery complete of the YY food of the XX restaurant, received through the food delivery service application.

In various embodiments, the processor 120 may receive the location information of the user's food intake. The location information may include POI information. The POI information may include the location of the electronic device 101. In various embodiments, the POI information may include information current area or location (e.g., a store, an institution, a facility, a building, etc.) information of the electronic device 101. In various embodiments, the POI information may include business name data of the store where the electronic device 101 is located. The processor 120 may determine the user's food intake by obtaining from the POI information, the place data corresponding to the location of the electronic device 101.

The place information may include sensing information. The sensing information may include data sensed at the place of the electronic device 101. In various embodiments, the sensing information may include information for identifying a device such as a base station, an AP, a beacon device, or an NFC device, at the place of the electronic device 101. Based on the information for identifying the device in the sensing information, the processor 101 may determine the place of the electronic device 101. The processor 120 may determine the user's food intake using the determined place information.

Figure 10:
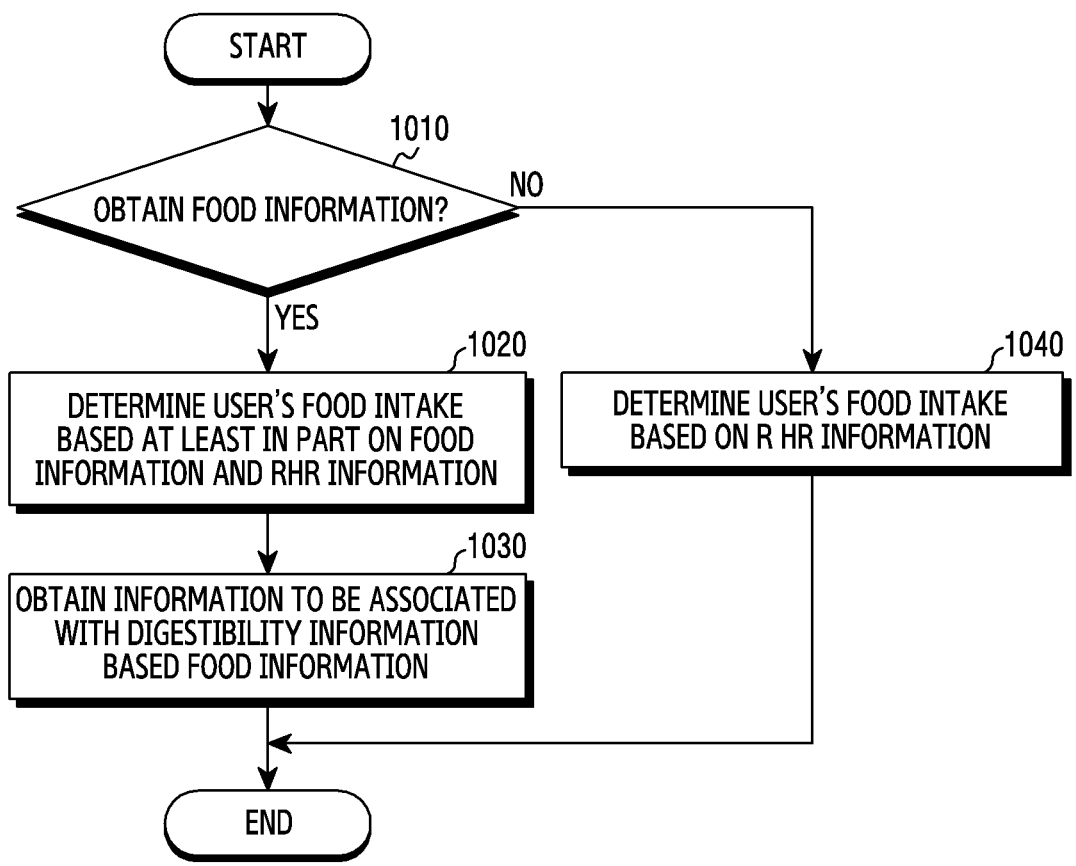
FIG. 10 illustrates an example of operations of an electronic device for determining user's food intake according to various embodiments.
Figure 11A:
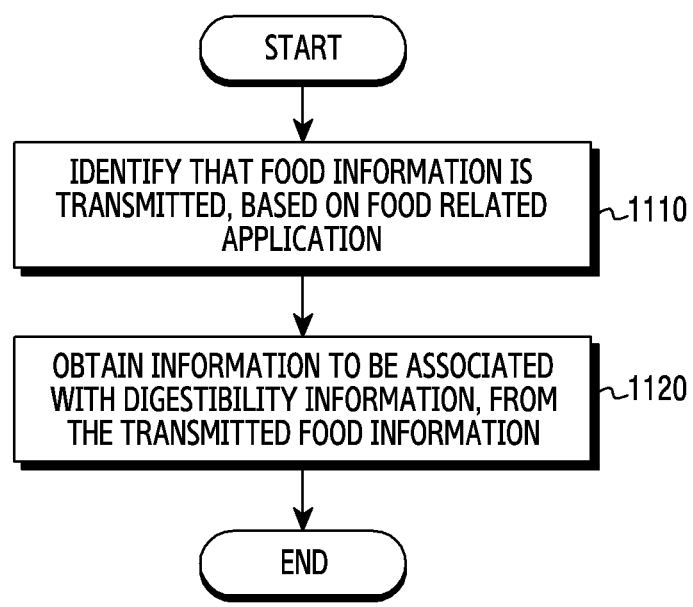
FIG. 11A illustrates an example of operations of an electronic device for obtaining information to be associated with digestibility information according to various embodiments.
Figure 11B:
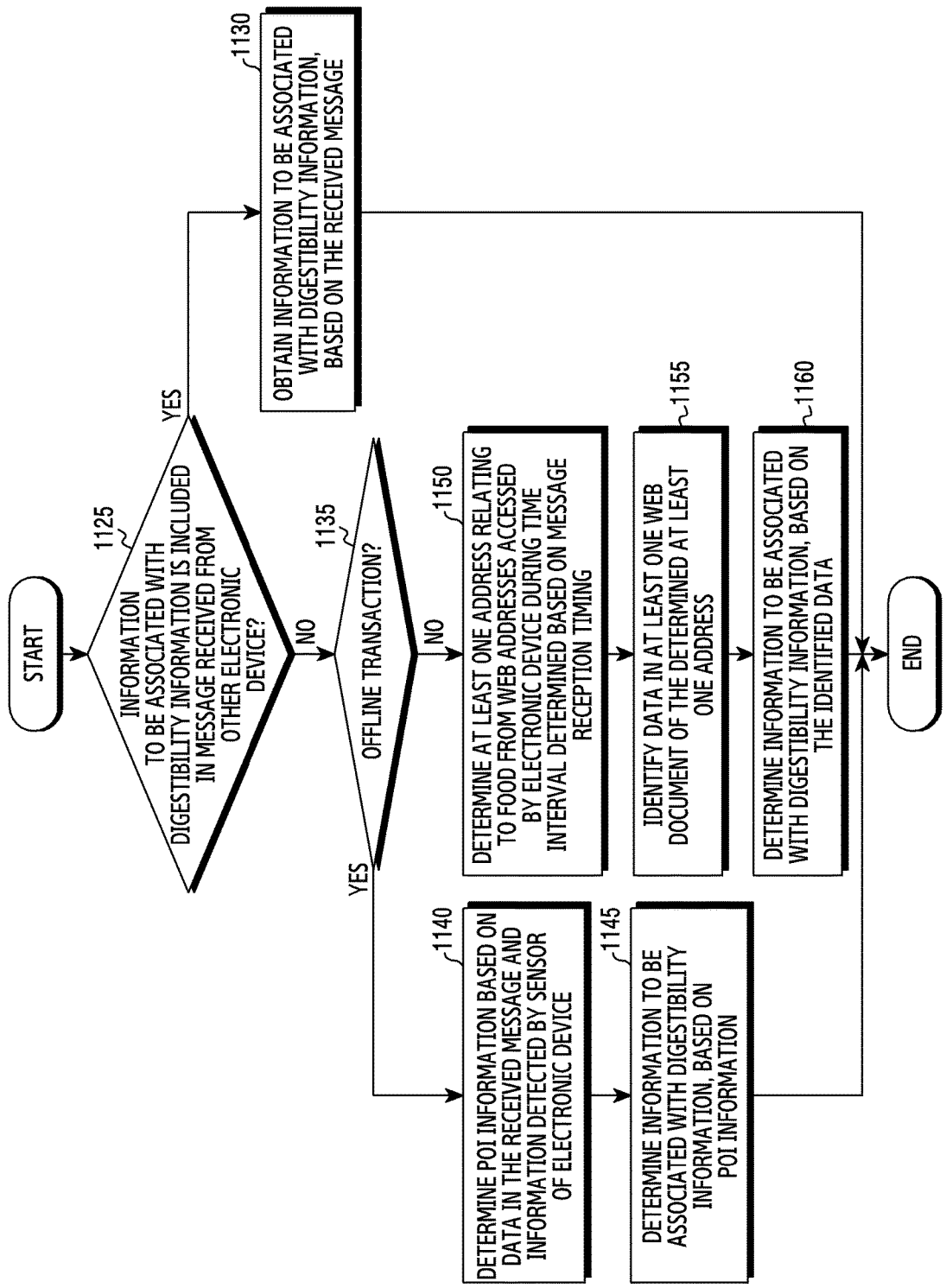
FIG. 11B illustrates an example of operations of an electronic device for obtaining information to be associated with digestibility information according to various embodiments.

Determining the user's food intake shall be described in further detail by referring to FIG. 10, FIG. 11A, and FIG. 11B.

In operation 730, the processor 120 may identify RHR changes. The processor 120 may identify the RHR changes using the digestibility determining instruction 630 stored in the memory 130. In various embodiments, in response to the user's food intake, the processor 120 may identify or monitor the RHR changes based on the obtained RHR information. By identifying the RHR changes, the processor 120 may identify timings, e.g. times when the RHR peaks to the time the RHR bottoms, for determining the digestibility in the obtained RHR information. In various embodiments, referring to FIG. 8, the processor 120 may monitor the RHR changes indicated by the graph 800 and thus identify a time "a" (e.g., a peak timing) at which the user RHR changes from increase to decrease. By monitoring the RHR changes indicated by the graph 800, the processor 120 may identify a timing "b" at which the user RHR changes from decrease to increase or reaches the RHR measured on the empty stomach. "b" may be a parameter for determining a completion of digestion time of the food taken by the user.

Unlike the graph 800 of FIG. 8, the RHR information might not include the time at which the RHR changes from increase to decrease or the time at which the RHR changes from decrease to increase. In various embodiments, if the user takes the food and keeps moving and accordingly the RHR is not measured at the timing "a" where the RHR changes from increase to decrease, the processor 120 may not obtain the time at which the RHR changes from increase to decrease, from the RHR information acquired through the ppg sensor 410. In this case, the processor 120 may estimate the time at which the RHR changes from increase to decrease, based on one or more of current RHR data, RHR information which has been stored in the electronic device 101, information acquired using the machine learning, or information according to statistical data. The statistical data may be provided from a big data server to the electronic device 101. In various embodiments, if the user moves in the time interval including the timing b where the RHR changes from decrease to increase or the timing b where the RHR reaches the same resting heart rate as measured on the empty stomach, the processor 120 may not obtain data of the timing where the RHR changes from decrease to increase or the timing where the RHR reaches the same resting heart rate as measured on the empty stomach, from the RHR information acquired through the ppg sensor 410. In this case, the processor 120 may estimate the data of the time b at which the RHR changes from decrease to increase or the time b where the RHR reaches the same resting heart rate as measured on the empty stomach, based on one or more of the current RHR data, the RHR information which has been stored in the electronic device 101, the information acquired using the machine learning, or the information according to the statistical data.

In operation 740, the processor 120 may determine the digestibility of the food taken by the user, based on the RHR changes. The processor 120 may determine the digestibility of the food taken by the user, using the digestibility determining instructions 630. The digestibility may be the parameter indicating the digestion rate of the food taken by the user. The digestibility may have a different value for each user. The digestibility may have a different value for each food eaten. In various embodiments, the digestibility may represent the food digestion rate according to the user's intake time. For example, the digestibility may have different values for the same food according to a breakfast time, a lunch time, or a dinner time.

The processor 120 may determine the digestibility based on the information identified in operation 730. In various embodiments, referring to FIG. 8, the processor 120 may determine the digestibility, based on the time "a" at which the RHR changes from increase to decrease, the RHR α at the time "a", the time b at which the RHR changes from decrease to increase or reaches the same resting heart rate as measured on the empty stomach, and the RHR β at the time b. The processor 120 may determine the digestibility based on Equation 1.

$$D = \left| \frac{\beta - \alpha}{b - a} \right| \quad (1)$$

In Equation 1, D denotes the digestibility, β denotes the RHR at the timing b, a denotes the RHR at the timing a, b denotes the timing at which the RHR changes from decrease to increase or reaches the same resting heart rate as measured on the empty stomach, and a denotes the timing at which the RHR changes from increase to decrease.

In various embodiments, the processor 120 may determine the digestibility using glucose level information acquired by the configuration for measuring the sugar. The glucose level information may be used to determine the digestibility of carbohydrates (for example, the glycemic index) in the food taken by the user. The processor 120 may determine the digestibility information using not only the RHR information but also the sugar level information.

In operation 750, the processor 120 may process the determined digestibility information. Using the digestibility processing instruction 635, the processor 120 may process the determined digestibility information.

The processor 120 may map digestibility based on the food. In various embodiments, the processor 120 may store the determined digestibility information. In various embodiments, the processor 120 may associate or map the determined digestibility information with the food taken by the user. In various embodiments, if determining that the user takes a food A in operation 720, the processor 120 may map the determined digestibility information to the food A, or associate the food A with the determined digestibility information in the memory. The processor 120 may store the digestibility information associated with the food taken by the user. In various embodiments, the processor 120 may store the digestibility information associated with the food A. The stored information may be used to determine an average digestibility of the food associated with the digestibility information. If the user re-takes the food associated with the digestibility information, the stored information may be used to determine an estimated digestion time of the food.

The processor 120 may map digestibility by user. In various embodiments, the processor 120 may map the determined digestibility information to the user who is identified through authentication. In various embodiments, if a user A is authenticated at the electronic device 101 (e.g., if the user A unlocks the electronic device 101), the processor 120 may map the determined digestibility information to the user A. In various embodiments, if a user B is authenticated at the electronic device 101, the processor 120 may map the determined digestibility information to the user B. The processor 120 may store the digestibility information associated with the user. In various embodiments, the processor 120 may store the digestibility information associated with the user A or the digestibility information associated with the user B. The stored information may indicate a health condition in relation to the user's digestion. The stored information may be used to determine the user's average digestibility.

In various embodiments, the processor 120 may generate digestibility related information based on the stored digestibility information. The digestibility related information may be obtained from the digestibility information. In an embodiment, based on the stored digestibility related information, the processor 120 may generate the time required to digest a particular food compared to the stored digestibility information. In another embodiment, based on the stored digestibility related information, the processor 120 may generate estimated digestion time information of a particular food in relation to the stored digestibility information. In yet another embodiment, the processor 120 may generate user's sleeping quality information, based on the stored digestibility information, intake timing (or time (e.g., breakfast, lunch, dinner)) information of the particular food associated with the stored digestibility information, and user sleep time information. In still another embodiment, the processor 120 may generate information for providing the user with the particular food associated with the stored digestibility information as an adequate food. In a further embodiment, the processor 120 may generate information, notification, or alarm for a recommended meal time based on the stored digestibility information. In a further embodiment, the processor 120 may generate glucose level measurement timing information, based on the stored digestibility information.

In various embodiments, the processor 120 may transmit one or more of the digestibility information or the digestibility related information to at least one other electronic device (e.g., the first external electronic device 102, the server 106). In various embodiments, the processor 120 may transmit one or more of the digestibility information or the digestibility related information to the external electronic device 102, in order to display one or more of the digestibility information or the digestibility related information at the external electronic device 102 which is associated with the electronic device 101 and related to the user. In various embodiments, to provide user's health information, the processor 120 may transmit one or more of the digestibility information or the digestibility related information to the server 106 such as a big data server or a healthcare server.

In various embodiments, the processor 120 may display one or more of the digestibility information or the digestibility related information. In various embodiments, in response to identifying that the designated condition is satisfied, the processor 120 may display one or more of the digestibility information or the digestibility related information.

Processing the digestibility information shall be described in detail by referring to FIG. 12 through FIG. 15D.

As such, the electronic device 101 according to various embodiments may determine the digestibility information of the food taken by the user based on the RHR information. By determining the digestibility information, the electronic device 101 may provide information for correcting user's eating habits or information for improving the user's health.

According to various embodiments, operation 720 may be omitted in some cases. For example, the processor 120 may determine the food intake based on the RHR changes and determine the digestibility, without the food intake information.

FIG. 9A illustrates an example of operations of an electronic device for determining a digestibility according to various embodiments and elaborates further on operations 730 and 740 of FIG. 7. The operations of FIG. 9A may be carried out by the electronic device 101 of FIG. 1, the electronic device 201 of FIG. 2, the electronic device 101 of FIG. 6, the component (e.g., the processor 120) of the electronic device 101, or the component (e.g., the processor 210) of the electronic device 201.

Operations 901 through 906 of FIG. 9A may be involved in operations 730 and 740 of FIG. 7.

Referring to FIG. 9A, in operation 901, the processor 120 may control the ppg sensor 410 to obtain signals for heart rate estimation. The processor 120 may obtain the signals for the heart rate estimation using the RHR measuring instruction 620. Based on the signals acquired through the ppg sensor 410, the processor 120 may obtain user's heart rate information.

In operation 902, the processor 120 may calculate the RHR while the user does not move. The processor 120 may calculate the RHR using the state determining instruction 625. In various embodiments, the processor 120 may obtain user's RHR information from the user heart rate information obtained in operation 901. As noted above, the ppg sensor 401 may normally be deactivated. Operation 902 may include activation of the ppg sensor 401.

In operation 903, based on the obtained RHR information, the processor 120 may determine a peak point and a valley point of the RHR. The processor 120 may determine the peak point and the valley point of the RHR, using the digestibility determining instruction 630. In various embodiments, the processor 120 may determine the peak point and the valley point by analyzing the obtained RHR information based on the time axis. The peak point may correspond to the timing a of FIG. 8, and the valley point may correspond to the timing b of FIG. 8.

In operation 904, the processor 120 may calculate a time difference between the times of the peak point and the valley point, and calculate an RHR difference between the peak point and the valley point. Using the digestibility determining instruction 630, the processor 120 may calculate the time difference of the peak point and the valley point and calculate the RHR difference between the peak point and the valley point. The RHR at the peak point may correspond to the RHR α of FIG. 8, and the RHR at the valley point may correspond to the RHR (3 of FIG. 8.

In operation 905, the processor 120 may determine a RHR difference, using the calculated time difference and the calculated RHR difference. The processor 120 may determine the RHR difference, using the digestibility determining instruction 630. If the RHR information is represented with the graph of FIG. 8, the difference may correspond to a slope.

In operation 906, the processor 120 may determine the calculated difference as the digestibility. Since the RHR may be used as the parameter of the user's digestion status, the calculated difference may be related to the digestibility indicating the user's digestion rate. The processor 120 may determine the digestibility using the digestibility determining instruction 630.

Although not depicted in FIG. 9A, the processor 120 may process the determined digestibility information. The processor 120 may update the user's digestibility information corresponding to the electronic device 101 by combining the digestibility information determined in operation 906 with digestibility information previously determined. In various embodiments, the processor 120 may compare the previous digestibility with the digestibility determined in operation 906. If a difference between the previous digestibility and the digestibility determined in operation 906 exceeds a designated value in the comparison, the processor 120 may discard the digestibility determined in operation 906. If the difference between the previous digestibility and the digestibility determined in operation 906 falls below the designated value in the comparison, the processor 120 may update the user's digestibility information based on the digestibility determined in operation 906.

FIG. 9B illustrates an example of operations of an electronic device for obtaining RHR information according to various embodiments and further elaborates on operation 710 of FIG. 7. The operations of FIG. 9B may be carried out by the electronic device 101 of FIG. 1, the electronic device 201 of FIG. 2, the electronic device 101 of FIG. 6, the component (e.g., the processor 120) of the electronic device 101, or the component (e.g., the processor 210) of the electronic device 201.

Operations 910, 920, and 930 of FIG. 9B may be involved in operation 710 of FIG. 7. Generally, operations 910, 920, and 930 determine whether the user is in a resting state.

Referring to FIG. 9B, in operation 910, the processor 120 may determine motion of the electronic device. The processor 120 may determine the motion of the electronic device 101 using the state determining instruction 625. To determine the motion of the electronic device 101, the processor 120 may control the state sensor 610. The motion of the electronic device 101 may correspond to a user movement state. In general, if the user is exerting themselves, or not in resting state, the motion of the electronic device 101 as measured by sensors will be high. Based on information obtained through the state sensor 910, the processor 120 may determine the movement state of the electronic device 101. In various embodiments, based on the information obtained through the state sensor 910, the processor 120 may determine that the user grips the electronic device 101. In various embodiments, based on the information obtained through the state sensor 910, the processor 120 may determine that the user does not carry the electronic device 101. If the user is not carrying the electronic device 101, a low motion of the electronic device would not be indicative of the resting state of the user. In various embodiments, based on the information obtained through the state sensor 910, the processor 120 may determine that the user carries the electronic device 101 but in the stationary state.

In operation 920, the processor 120 may determine whether the determined state satisfies a designated condition. The designated condition may be used to determine whether the user of the electronic device 101 is at rest (or enables the RSR measurement). The designated condition may differ per user (for example, based on the physical activity common to the user, previously known health issues of the user, and demographics, such as the age, of the user). The designated condition may be set through machine learning. In various embodiments, the designated condition may indicate that the user wears or carries the electronic device 101 and maintains the movement smaller than a reference movement during a designated time.

If the determined state satisfies the designated condition, the processor 120 may perform operation 930. By contrast, if the determined state does not satisfy the designated condition, the processor 120 may return to operation 910. In various embodiments, unlike FIG. 9B, if the determined state does not satisfy the designated condition, the processor 120 may stop determining the digestibility (e.g., stop operations 730, 740, and 750).

In response to determining that the determined state satisfies the designated condition, the processor 120 may obtain RHR information in operation 930. The processor 120 may obtain the RHR information using the RHR measuring instruction 620. In various embodiments, in response to determining that the determined state satisfies the designated condition, the processor 120 may obtain the RHR information in the heart rate information acquired through the ppg sensor 410. In various embodiments, in response to determining that the determined state satisfies the designated condition, the processor 120 may activate the ppg sensor 410. The processor 120 may acquire the RHR information through the activated ppg sensor 410. Operation 930 can include activating a deactivated ppg sensor 410.

As above, the electronic device 101 according to various embodiments may identify whether the RHR is measurable, by monitoring the movement of the electronic device 101. In response to identifying that the movement state of the electronic device 101 satisfies the designated condition according to the monitoring, the electronic device 101 may measure the RHR.

FIG. 10 illustrates an example of operations of an electronic device for determining user's food intake according to various embodiments and describes operation 720 in more detail. The operations of FIG. 10 may be carried out by the electronic device 101 of FIG. 1, the electronic device 201 of FIG. 2, the electronic device 101 of FIG. 6, the component (e.g., the processor 120) of the electronic device 101, or the component (e.g., the processor 210) of the electronic device 201.

Operations 1010 through 1040 of FIG. 10 may be involved in operation 720 of FIG. 7.

Referring to FIG. 10, in operation 1010, the processor 120 may identify whether food information is obtained. In various embodiments, the processor 120 may identify whether the food information is obtained from at least one other electronic device through the communication interface 170. The food information may include payment information of a food taken by the user, place information of the user's food intake, information occurred by a food related application, and so on. By monitoring information transmitted or received through the communication interface 170, the processor 120 may identify whether the food information is obtained.

If the food information is obtained, the processor 120 may perform operation 1020. By contrast, if the food information is not obtained during operation 1020, the processor 120 may perform operation 1040.

In response to a determination that the food information was obtained during operation 1010, the food information, the processor 120 may determine user's food intake based at least in part on the food information and RHR information in operation 1020. In various embodiments, the processor 120 may determine user's food intake based on the food payment information of the food information. In various embodiments, the processor 120 may determine user's food intake, by identifying RHR increase based on the RHR information.

In operation 1030, the processor 120 associates the food information with the digestibility information. The processor 120 may obtain information to be associated with the digestibility information based the food information. In various embodiments, if the food information includes information about a food type taken by the user, the processor 120 may obtain the food type information of the user as the information to be associated with the digestibility information. In various embodiments, if the food information includes the place information of the user's food intake, the processor 120 may obtain the place information as the information to be associated with the digestibility information.

Operation 1020 and operation 1030 may be conducted at the same time or in any order.

In response to no food information obtained, the processor 120 may determine the user's food intake based on the RHR information in operation 1040. In various embodiments, the processor 120 may determine the user's food intake, by identifying the RHR increase based on the RHR information acquired through the ppg sensor 410.

As such, the electronic device 101 according to various embodiments may determine the user's food intake, based at least in part on the RHR information and the food information. If obtaining the food information, the electronic device 101 may obtain information to be mapped to the digestibility information based on data in the food information. Using the obtained information, the electronic device 101 may generate digestibility related information when processing the digestibility information in operation 750.

FIG. 11A illustrates an example of operations of an electronic device for obtaining information to be associated with digestibility information according to various embodiments and illustrates operation 1030 in more detail. The operations of FIG. 11A may be carried out by the electronic device 101 of FIG. 1, the electronic device 201 of FIG. 2, the electronic device 101 of FIG. 6, the component (e.g., the processor 120) of the electronic device 101, or the component (e.g., the processor 210) of the electronic device 201.

Operations 1110 and 1120 of FIG. 11A may be related to operation 1030 of FIG. 10.

Referring to FIG. 11A, in operation 1110, the processor 120 may identify that food information is transmitted, based on a food related application. The food related application may be a food delivery service application. The food related application may be a food ordering application using Internet. The food information may include data about a food type (e.g., a menu) ordered by the user. The food information may include restaurant data of the food ordered by the user. The food information may include data of a food amount (e.g., sushi eight pieces, one noodle, a large-size pizza, etc.) ordered by the user. The processor 120 may identify that the food information is transmitted to the server 106, by monitoring information transmitted through the food related application.

In operation 1120, the processor 120 may obtain information to be associated with the digestibility information, from the transmitted food information. In various embodiments, the processor 120 may obtain the information to be associated with the digestibility information by identifying the transmitted food information. In various embodiments, by identifying the transmitted food information, the processor 120 may obtain the ordered food type data as the information to be associated with the digestibility information. In various embodiments, by identifying the transmitted food information, the processor 120 may obtain the ordered food amount data as the information to be associated with the digestibility information. If the user orders foods for several persons, the processor 120 may display on the display 160 a message inquiring about the menu and the amount of the food eaten by the user among the ordered foods. In response to a user input based on the displayed message, the processor 120 may determine the food and the amount eaten by the user, with the food and the amount which are input by the user. In various embodiments, by identifying the transmitted food information, the processor 120 may obtain the restaurant data of the user's ordered food as the information to be associated with the digestibility information. However, the information to be associated with the digestibility information obtained from the transmitted food information is not limited those.

FIG. 11B illustrates an example of operations of an electronic device for obtaining the information to be associated with the digestibility information according to various embodiments. The operations of FIG. 11B may be carried out by the electronic device 101 of FIG. 1, the electronic device 201 of FIG. 2, the electronic device 101 of FIG. 6, the component (e.g., the processor 120) of the electronic device 101, or the component (e.g., the processor 210) of the electronic device 201.

Operations 1125 through 1160 of FIG. 11B may be related to operation 1030 of FIG. 10.

Referring to FIG. 11B, in operation 1125, the processor 120 may identify whether the information to be associated with the digestibility information is included in a message received from other electronic device. The message may be received at the electronic device 101 from the external electronic device 102 or the server 106. In various embodiments, the message may be received from a payment server. The message may include information indicating that a transaction of the electronic device 101 is completed. In various embodiments, the message may include payment information of the food taken by the user.

In various embodiments, the processor 120 may identify data in the message. The processor 120 may identify based on the identified data whether the information to be associated with the digestibility information is obtainable. If the identified data contains the information to be associated with the digestibility information, the processor 120 may perform operation 1130. By contrast, if the identified data does not contain the information to be associated with the digestibility information, the processor 120 may perform operation 1135.

If the message contains the information to be associated with the digestibility information, the processor 120 may obtain the information to be associated with the digestibility information, from the message in operation 1130. In various embodiments, the electronic device 101 may obtain information about the food type taken by the user, the food amount taken by the user, and the food purchase place, from the identified data. In various embodiments, the processor 120 may obtain the information to be associated with the digestibility information, using only the identified data. In various embodiments, to supplement the determined information based on the identified data, the processor 120 may access a website obtained from the identified data or a big data server. In this case, the processor 120 may acquire the information to be associated with the digestibility information by combining at least part of data in the accessed website, data in the big data server, and the identified data. However, obtaining the information to be associated with the digestibility information is not limited this method.

If the message does not include the information to be associated with the digestibility information, the processor 120 may identify or determine whether the food transaction is conducted offline in operation 1135. Off-line can include obtaining food without using the electronic device 101. In various embodiments, the processor 120 may identify whether the food transaction is conducted offline, based on the identified data in operation 1125. In various embodiments, based on food source information (e.g., XX restaurant, YY online mart, etc.) in the identified data, the processor 120 may identify whether the user orders the food online and takes the food offline. If the food transaction is offline, the processor 120 may perform operation 1140. By contrast, if the food transaction is online, the processor 120 may perform operation 1150.

If the food transaction is offline, the processor 120 may determine POI information based on the data in the received message and information detected by the sensor module 240 in operation 1140.

In various embodiments, the processor 120 may determine brief information of the information to be associated with the digestibility information, using the data identified in operation 1125. In various embodiments, using the identified data, the processor 120 may specify "the price of the food is $12.00", "the food transaction place is Y coffee shop in Gangnam-gu, Korea", and so on.

In various embodiments, the processor 120 may determine sensing information using the sensor module 240 or the communication interface 170. In various embodiments, the sensing information may be coordinate data of a point of the electronic device 101, which is acquired by a GPS of the electronic device 101. In various embodiments, the sensing information may be data in a signal received through the communication interface 170 of the electronic device 101. The data in the sensing information may include media access control (MAC) address data of other electronic device (e.g., a base station, an AP, a Bluetooth signal transmitter, etc.) or data (e.g., an identifier (ID) of the other electronic device) for identifying the other electronic device, in the received signal. Based on the sensing information, the processor 120 may specify the information to be associated with the digestibility information. In various embodiments, the processor 120 may transmit the sensing information to the POI server of the electronic device 101. The processor 120 may request POI information relating to the sensing information from the POI server. The POI server may determine the POI information relating to the sensing information using data stored therein, and transmit the determined POI information to the electronic device 101. In various embodiments, the POI server may compare the MAC address of the sensing information with information stored in the POI server. Based on the comparison, the POI server may determine that the place of the electronic device 101 is "Y coffee shop second place in Gangnam-gu". The POI server may transmit to the electronic device, data indicating that the place of the electronic device 101 is "Y coffee shop second place in Gangnam-gu". However, the method of the electronic device 101 is not limited to this.

The processor 101 may determine the POI information of the food based at least in part on the identified data, the data received from the POI server, or their combination.

In operation 1145, the processor 120 may determine the information to be associated with the digestibility information, based on the determined POI information and further based on the price of the order. By analyzing the determined POI information, the processor 120 may recognize that the food related place is "Y coffee shop second place in Gangnam-gu" and the food price is $12.00. Based on the recognized information, the processor 120 may determine that the only food sold for $12.00 at the Y coffee shop second place in Gangnam-gu is a "turkey sandwich". Also, based on the recognized information, the processor 120 may determine that the food sold for $12.00 at the Y coffee shop second place in Gangnam-gu is "green-tea frappuccino" or "white chocolate mocha". In this case, the processor 120 may display on the display 160 a message inquiring about which one of "green-tea frappuccino" and "white chocolate mocha" is taken. The processor 120 may determine the food "green-tea frappuccino" in response to a user input for selecting "green-tea frappuccino" in the displayed message.

In other words, using one or more of the message received from the payment server, the information collected by the processor 120, or the information received from the POI server, the processor 120 may determine the food type information, the food place information, or the food amount information, as the information to be associated with the digestibility information.

If the food transaction is online, the processor 120 may determine at least one, which corresponds to at least one reference address in relation to the food, of web addresses accessed by the electronic device 101 during a time interval determined based on the message reception timing in operation 1150. The time interval may range from a particular time before the message reception timing, to the message reception timing. The reference address may be an address pre-stored in the electronic device 101. The reference address may be used to identify which one of the web addresses is related to the food. In various embodiments, the reference address may be "www.0000chicken.com", "www.XXYYpizza.com", "www.KKKKnoodle.com", and so on. The reference address may be stored in the electronic device 101 at the phase of release or update of the electronic device 101, received from the big data server, or stored according to learning of the electronic device 101.

The processor 120 may select web addresses accessed for the time interval from the web addresses accessed by the electronic device 101, compare the selected web addresses with the at least one reference address, and thus determine at least one address regarding the food. In various embodiments, the processor 120 may select web addresses A(1), A(k−1), A(k), A(k+1), A(n−1), and A(n) accessed by the electronic device 101 during the time interval among the web addresses A(1), A(k), . . . , A(n) accessed by the electronic device 101, and compare the selected web addresses A(1), A(k−1), A(k), A(k+1), A(n−1), and A(n) with reference addresses B(1), B(2), B(3), and B(4) stored in the electronic device 101. The processor 120 may determine that A(k−1), A(k), A(k+1) correspond to at least one of the reference addresses B(1), B(2), B(3), and B(4), and A(1), A(n−1), and A(n) do not correspond to the reference addresses B(1), B(2), B(3), and B(4). That is, the processor 120 may determine A(k−1), A(k), A(k+1) as the food related address.

In operation 1155, the processor 120 may identify data in at least one web document of the determined at least one address.

In various embodiments, the web document may be in a document object model (DOM) tree format. The processor 120 may identify the data in the at least one web document using rule-based parsing (parser tool or library) or the machine learning. The identified data may include a common tag.

In operation 1160, the processor 120 may determine the information to be associated with the digestibility information, based on the identified data. In various embodiments, the processor 120 may extract the common tag from the identified data. The common tag may include, but not limited to, food image data, food source data, food price data, food type data, and the like. The processor 120 may compare the data of the common tag with the data of the received message, and thus determine the food information as the information to be associated with the digestibility information.

According to embodiments, the processor 120 may perform other operation different from operations 1150, 1155, and 1160. In various embodiments, in response to the online transaction in operation 1135, the processor 120 may display a message, as a pop-up window, inquiring about one or more of the type or the amount of the food ordered or taken by the user. Based on a user input for the message, the processor 120 may determine one or more of the food type or the food amount as the food information. The processor 120 may determine the food information as the information to be associated with the digestibility information.

Although not depicted in FIG. 11B, the information to be associated with the digestibility information may be used to generate or determine the digestibility related information.

As such, the electronic device 101 according to various embodiments may determine the information to be associated with the digestibility information, based on at least one of the received message, the POI data, or the identified data for the web document data.

Although not depicted in FIG. 11A and FIG. 11B, the processor 120 may map the information to be associated with the digestibility information to the digestibility information. The processor 120 may store the mapped information. In various embodiments, the processor 120 may update the stored digestibility information with the information to be associated with the digestibility information.

Figure 12:
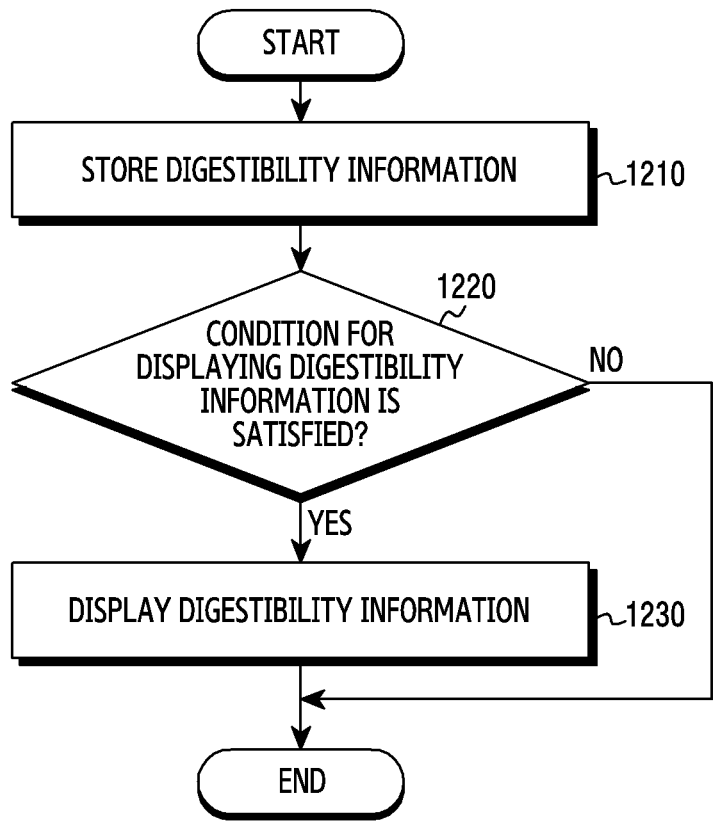
FIG. 12 illustrates an example of operations of an electronic device for processing digestibility information according to various embodiments.
Figure 13A:
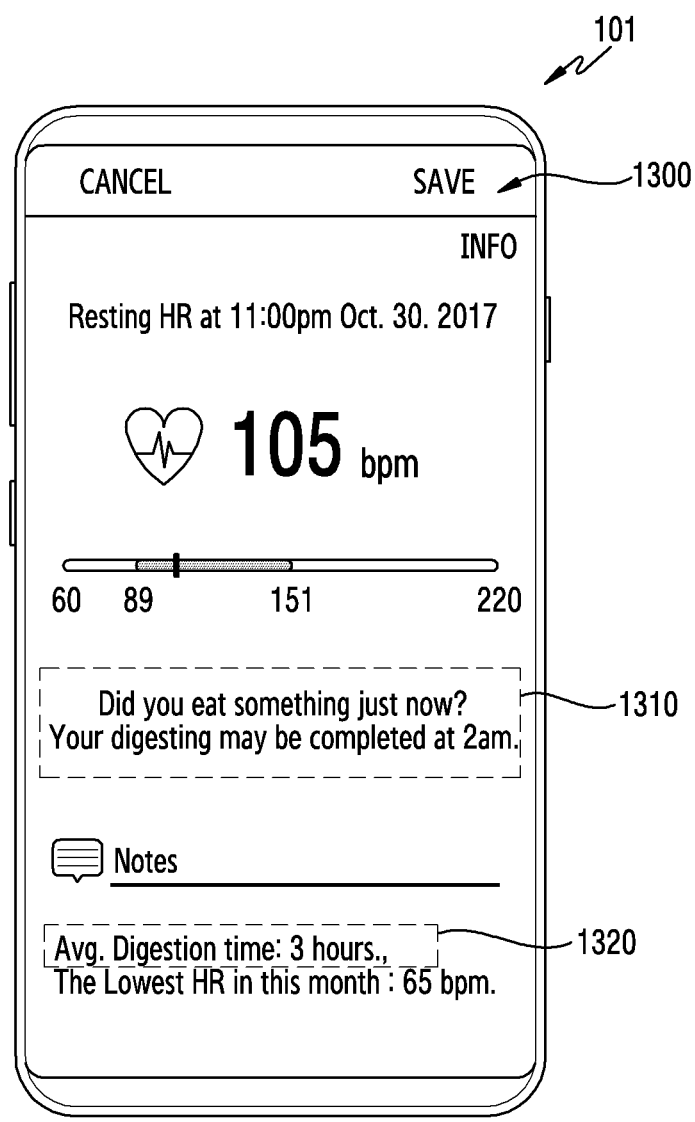
FIG. 13A, FIG. 13B, and FIG. 13C illustrate an example of a user interface (UI) which represents digestibility information.
Figure 13B:
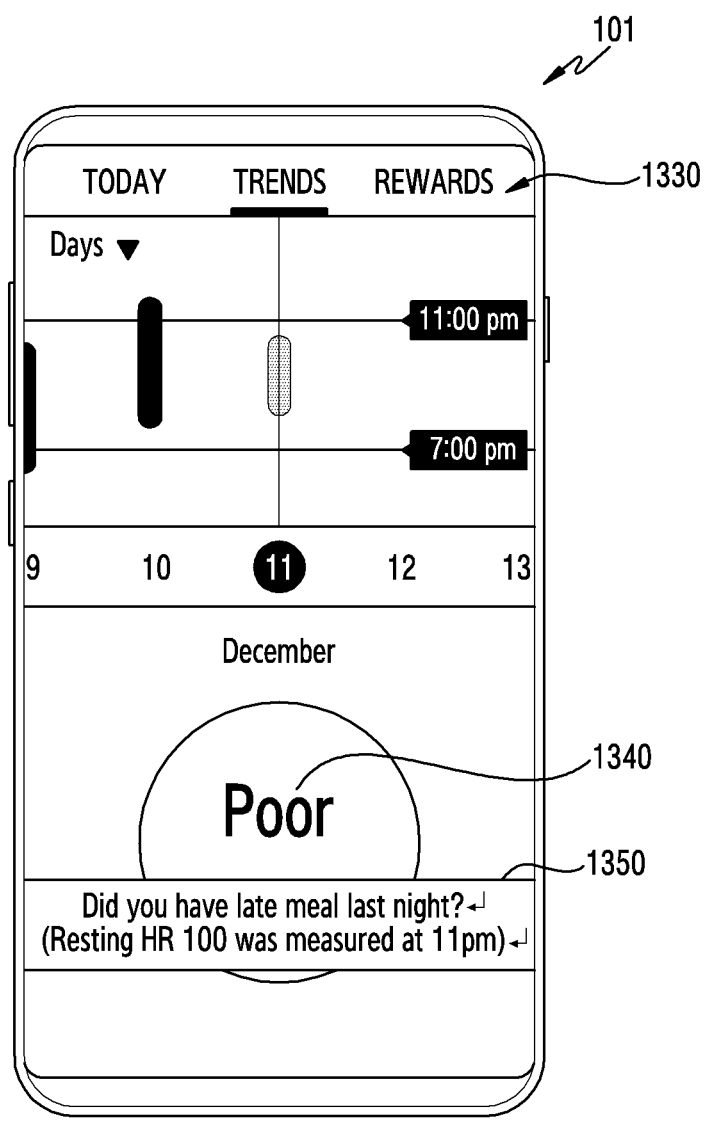
Figure 13C:
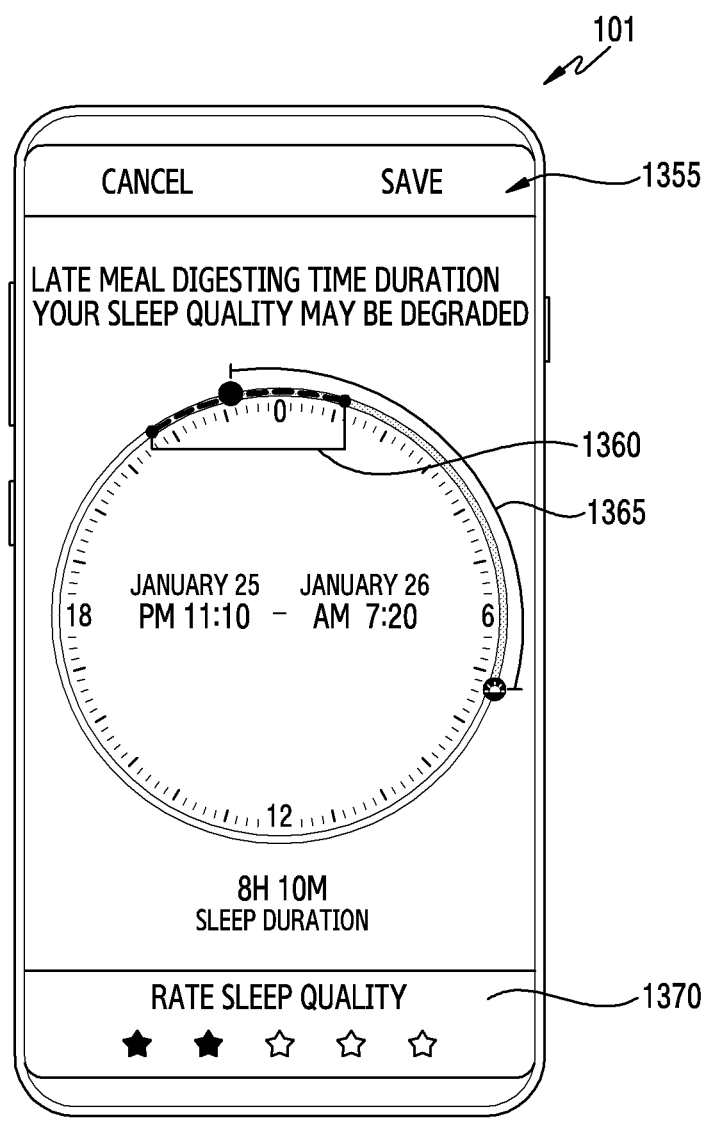

FIG. 12 illustrates an example of operations of an electronic device for processing digestibility information according to various embodiments. FIGS. 13A, 13B, and 13C illustrate an example of a UI which represents digestibility information. The operations of FIG. 12 may be carried out by the electronic device 101 of FIG. 1, the electronic device 201 of FIG. 2, the electronic device 101 of FIG. 6, the component (e.g., the processor 120) of the electronic device 101, or the component (e.g., the processor 210) of the electronic device 201.

Referring to FIG. 12, in operation 1210, the processor 120 may store the digestibility information. The processor 120 may store the digestibility information, using the digestibility processing instruction 635. In various embodiments, the processor 120 may store the digestibility information, in order to display the digestibility information. The stored digestibility information may be divided based on the timing or the time zone (e.g., breakfast, lunch, dinner, etc.) when the user takes the food. In various embodiments, the processor 120 may store the digestibility information, to provide the digestibility information to other electronic device. In various embodiments, the processor 120 may store the digestibility information, to generate the digestibility related information based on the digestibility information.

In operation 1220, the processor 120 may identify whether a condition for displaying the digestibility information is satisfied. The condition for displaying the digestibility information can be set variously. In various embodiments, the condition for displaying the digestibility information may indicate arrival of a designated period. In various embodiments, the condition for displaying the digestibility information may be determined according to user setting.

In various embodiments, if the user takes the food at time interrupting deep sleep, the processor 120 may identify that the condition for displaying the digestibility information is satisfied. In various embodiments, at time for displaying user's health information, the processor 120 may identify that the condition for displaying the digestibility information is satisfied.

In response to identifying that the condition for displaying the digestibility information is satisfied, the processor 120 may perform operation 1230.

In operation 1230, the processor 120 may display the digestibility information. The processor 120 may display the digestibility information, using the digestibility processing instruction 635. In various embodiments, displaying the digestibility information may directly display a digestibility value. In various embodiments, displaying the digestibility information may indirectly display the digestibility value.

FIGS. 13A, 13B, and 13C illustrate user interfaces displaying digestibility information.

In various embodiments, referring to FIG. 13A, the processor 120 may control the display 160 to display a UI 1300 as the digestibility information. The UI 1300 may the RHR, and messages 1320, and 1330 indicating digestibility information. The UI may provide include information indicating that the RHR is 105 at 11:00 PM on Oct. 30, 2017. The UI 1300 may include a message 1310, as the digestibility information, indicating that food digestion may be completed at 2:00 AM if the user takes a food now. The estimated digestion timing displayed in the message 1310 may be classified per time zone and determine based on the stored digestibility information from previous measurements. The UI 1300 may include a message 1320, as the digestibility information, indicating that average food digestion time is three hours. According to embodiments, the average food digestion time may be classified per time zone and determine based on the stored digestibility information.

In various embodiments, referring to FIG. 13B, the processor 120 may control the display 160 to display a UI 1330 as the digestibility information based on trends and sleeping information. The UI 1330 may be used to provide sleeping quality information on daily basis. The UI 1330 may provide daily sleep time information in December. The UI 1330 may include a message 1340 indicating "poor" sleeping quality of December 11th. The UI 1330 may include a message 1350, as the digestibility information, indicating that a late meal causes the poor sleeping quality of December 11th.

In various embodiments, referring to FIG. 13C, the processor 120 may control the display 160 to display a UI 1335 as the digestibility information. The UI 1355 may be used to provide sleeping quality information from January 25th to January 26th. The UI 1355 may display an arc 1365 indicating a user's sleep time and an arc 1360 indicating a user's food digestion time. The arc 1360 may be highlighted, compared with the arc 1365. In various embodiments, the arc 1360 may be display thicker than the arc 1365 or in a different color from the arc 1365. With a message indicating that the late meal interrupting the user's sleeping quality is digested, the UI 1355 may include a notification 1370 for rating the sleeping state.

As such, the electronic device 101 according to various embodiments may display the digestibility information. By displaying the digestibility information, the electronic device 101 may provide the user health information, the user sleeping state information, and the user's eating habits information.

Figure 14:
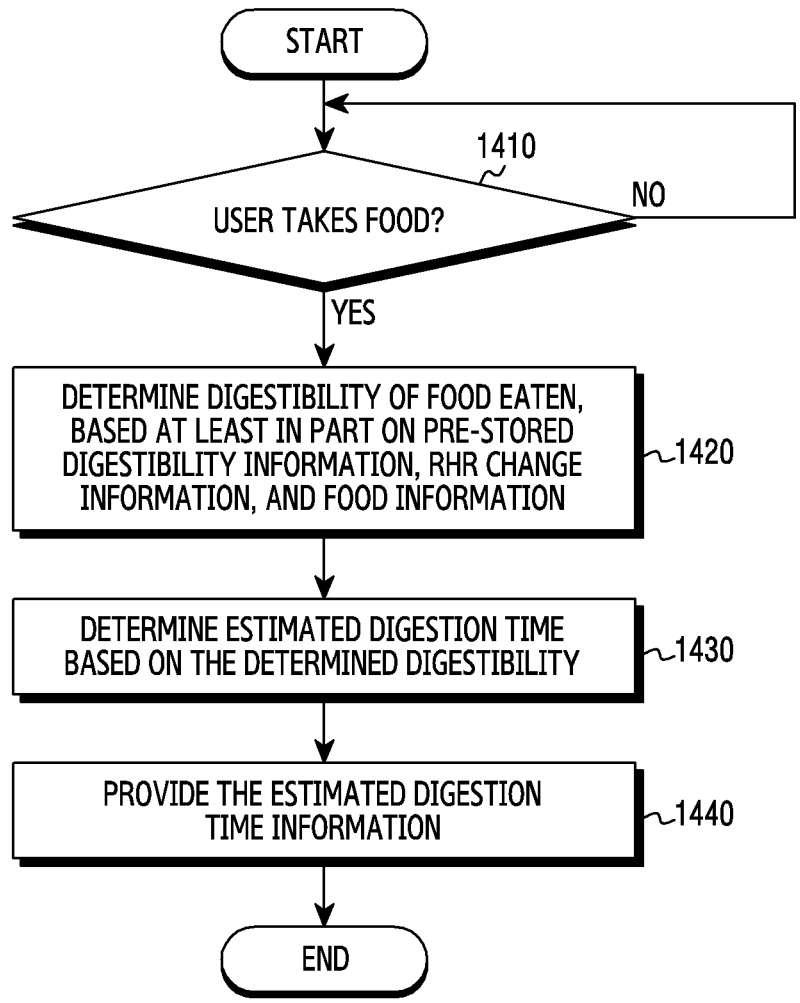
FIG. 14 illustrates another example of operations of an electronic device for processing digestibility information according to various embodiments.

FIG. 14 illustrates another example of operations of an electronic device for processing digestibility information according to various embodiments. FIGS. 15A through 15D illustrate an example of a UI which provides estimated digestion time information. The operations of FIG. 14 may be carried out by the electronic device 101 of FIG. 1, the electronic device 201 of FIG. 2, the electronic device 101 of FIG. 6, the component (e.g., the processor 120) of the electronic device 101, or the component (e.g., the processor 210) of the electronic device 201.

Referring to FIG. 14, in operation 1410, the processor 120 may determine whether user consumes food. In various embodiments, the processor 120 may determine whether the user consumes the food, based at least in part on user RHR information and food information.

If the user takes the food, the processor 120 may perform operation 1420. By contrast, if the user does not consume food, the processor 120 may return to operation 1410.

If the user takes the food, the processor 120 may determine a digestibility of the food taken by the user, based at least in part on pre-stored digestibility information, RHR change information, and food information in operation 1420. In various embodiments, the processor 120 may calculate an average digestibility of the food based on the pre-stored digestibility information associated with the food taken by the user, and combine the calculated average digestibility with RHR change information currently measured. Based on the combination, the processor 120 may determine or estimate the digestibility of the food taken by the user.

In operation 1430, the processor 120 may determine an estimated digestion time based on the determined digestibility. Since the determined digestibility indicates the digestibility rate of the food taken by the user, the processor 120 may determine the estimated digestion time using the determined digestibility.

In operation 1440, the processor 120 may provide information of the estimated digestion time. In various embodiments, in response to determining the estimated digestion time, the processor 120 may provide the estimated digestion time information. In various embodiments, to provide the estimated digestion time information, the processor 120 may directly display the estimated digestion time.

Figure 15A:
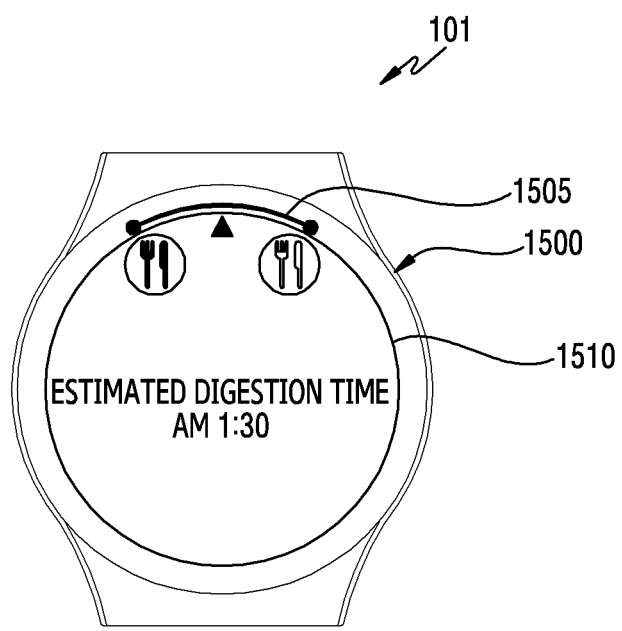
FIG. 15A, FIG. 15B, FIG. 15C and FIG. 15D illustrate an example of a UI which provides information of an estimated digestion time.

Referring to FIG. 15A, the processor 120 may display a UI 1500 on the display 160. The UI 1500 may be used to represent the estimated digestion time. The UI 1500 may include a progress bar 1505 representing the digestion degree of the food taken by the user. The UI 1500 may include a message indicating the digestion time information (e.g., the estimated digestion time 1:30 AM) 1510 of the food taken by the user.

Figure 15B:
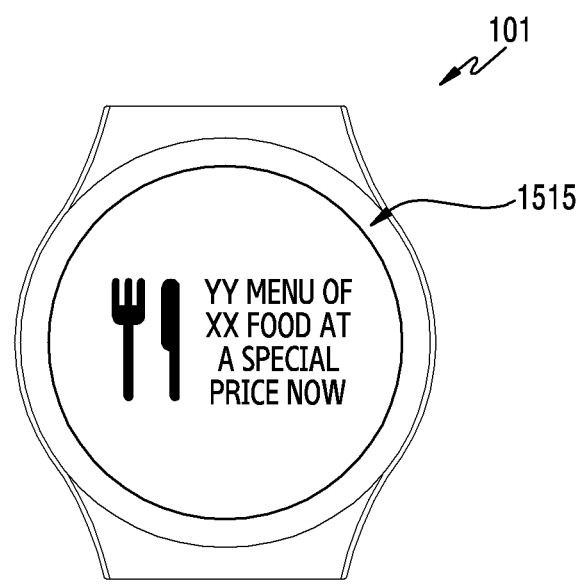

In various embodiments, to provide the estimated digestion time information, the processor 120 may display an advertising message to promote the user's food intake at the estimated digestion time of the food. Referring to FIG. 15B, in response to arrival of the estimated digestion time of the food, the processor 120 may display an advertising message 1515. The advertising message 1515 may display a source of the food at a special price. In various embodiments, the advertising message 1515 may further include link information associated with a site for purchasing the food of the special price.

Figure 15C:
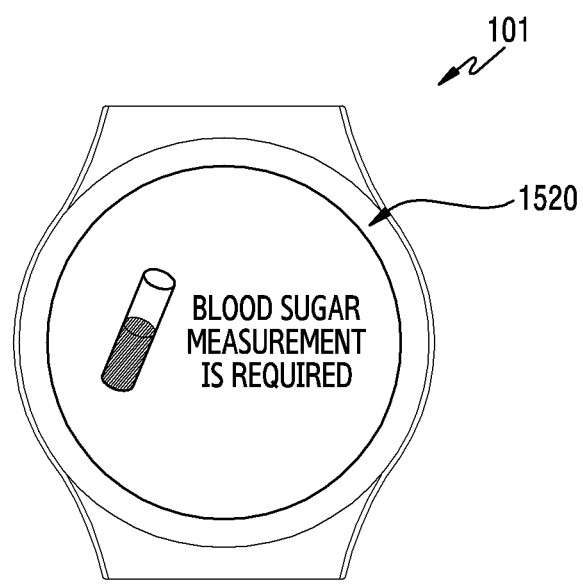

In various embodiments, to provide the estimated digestion time information, the processor 120 may display a notification message to lead user's glucose measurement at a timing requiring the glucose measurement because the digestion is completed. Referring to FIG. 15C, in response to the timing requiring the glucose measurement, the processor 120 may display a notification message 1520. The notification message 1520 may indicate the glucose measurement required. In various embodiments, if the electronic device 101 includes the configuration for measuring the glucose level, the processor 120 may measure the glucose level using the sugar measuring configuration, instead of displaying the notification message 1520.

Figure 15D:
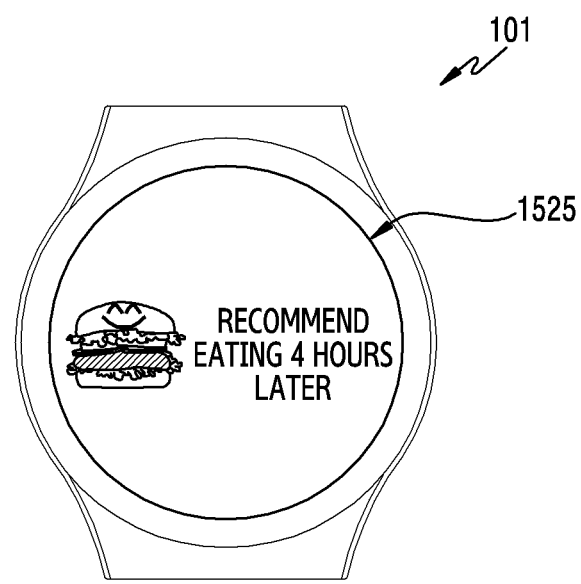

In various embodiments, to provide the estimated digestion time information, the processor 120 may display a message to correct user's inadequate eating habits or to prevent user's overeating. Referring to FIG. 15D, the processor 120 may display a message 1525 indicating a recommended meal time determined based on the estimated digestion time. The message 1525 may include contents recommending having a meal after a specific time.

As such, the electronic device 101 according to various embodiments may provide the user health service by displaying various information using the digestibility information. In various embodiments, the electronic device 101 may provide a service for improving the user health, a service for correcting the user's eating habits, a service for user's security, and so on.

As stated above, a method of a wearable device according to various embodiments may include obtaining food intake information of a user corresponding to the wearable device, obtaining biometric information of the user by using the biometric sensor, identifying a digestibility of the food of the user, based at least in part on a difference of the biometric information corresponding to the food intake information, and providing information of the digestibility, using the output device.

In various embodiments, the digestibility information may include duration of the food intake. The duration of the food intake may be determined based at least in part on a time at which the biometric information changes from peaks and a timing at which the biometric information bottoms out or reaches the biometric information measured on an empty stomach, or determined based on one or more of payment for food received from an external electronic device or information occurred by a particular application.

In various embodiments, the biometric information may include heart rate of the user.

In various embodiments, providing the digestibility information may include providing, based at least in part on the digestibility, sleeping information of the user as at least portion of the digestibility information.

According to various embodiments, a method of a wearable device may include obtaining resting heart rate information of the user through the one or more sensor, determining user food intake, based at least in part on the obtained information, identifying, in response to the determination, a change of the resting heart rate from the obtained resting heart rate information, determining a digestibility of the food taken by the user, based on the change of the resting heart rate, and storing the digestibility information in the memory.

In various embodiments, identifying the resting heart rate change may include identifying, from the resting heart rate information, a first timing at which the resting heart rate changes from increase to decrease and a second timing at which the resting heart rate changes from decrease to increase or reaches a resting heart rate measured on an empty stomach, and determining the digestibility, based on the first timing and the second timing. In various embodiments, the digestibility may be determined based at least in part on a resting heart rate value at the first time, a resting heart rate value at the second time, and time between the first timing and the second timing.

In various embodiments, the method may further include determining, if obtaining the resting heart rate information of the user, a sleeping quality of the user based on the digestibility, and displaying information of the sleeping quality through the display.

In various embodiments, the method may further include transmitting the digestibility information to an electronic device associated with the wearable device through the communication interface.

In various embodiments, the method may further include receiving food information from the electronic device associated with the wearable device, and determining the user food intake, based on the food information and the obtained information.

In various embodiments, one or more sensors of the wearable device may include one or more first sensors configured to obtain movement information of the user, and one or more second sensors configured to obtain the heart rate information of the user, wherein obtaining the resting heart rate information may include obtaining, in response to identifying that a difference of the user movement obtained through the one or more first sensors falls within a designated range, the resting heart rate information through the one or more second sensors. In various embodiments, the one or more first sensors may include one or more of an image sensor, a proximity sensor, a gyro sensor, or an acceleration sensor, and the one or more second sensors may include one or more of an ECG sensor, a PPG sensor, or a BCG sensor.

In various embodiments, the one or more sensors of the wearable device may include one or more first sensors configured to obtain movement information of the user, and one or more second sensors configured to obtain heart rate information of the user, wherein obtaining the resting heart rate information may further include switching, in response to identifying that a change of the user movement obtained through the one or more first sensors falls within a designated range, an operation state of the one or more second sensors from an idle state to an active state.

In various embodiments, the one or more sensors of the wearable device may include a PPG sensor and a film disposed over the PPG sensor.

In various embodiments, the method of the wearable device may further include obtaining the digestibility information corresponding to the food through the communication interface, storing the digestibility information in the memory, receiving information indicating the user food intake, from an external electronic device, and in response to identifying the user food intake corresponding to the stored digestibility information from the received information, determining an estimated digestion time of the food, based on the stored digestibility information. In various embodiments, the method may further include displaying information of the determined estimated digestion time in the form of a progress bar. In various embodiments, the method of the wearable device may further include transmitting the determined estimated digestion time information to the external electronic device.

According to various embodiments, a method of an electronic device may include obtaining information of a food taken by a user of the electronic device, obtaining information of a resting heart rate of the user from a wearable device associated with the electronic device, determining a digestibility of the food based at least in part on the food information and the resting heart rate information, and providing digestibility information.

In various embodiments, the method of the electronic device may further include transmitting a signal for providing the digestibility information in the wearable device.

In various embodiments, the method of the electronic device may further include providing, based at least in part on the digestibility, user sleeping information as at least portion of the digestibility information.

The methods according to the embodiments described in the claims or the specification of the present disclosure may be implemented in software, hardware, or a combination of hardware and software.

As for the software, a computer-readable storage medium storing one or more programs (software modules) may be provided. One or more programs stored in the computer-readable storage medium may be configured for execution by one or more processors of an electronic device. One or more programs may include instructions for controlling the electronic device to execute the methods according to the embodiments described in the claims or the specification of the present disclosure.

Such a program (software module, software) may be stored to a random access memory, a non-volatile memory including a flash memory, a read only memory (ROM), an electrically erasable programmable ROM (EEPROM), a magnetic disc storage device, a compact disc (CD)-ROM, digital versatile discs (DVDs) or other optical storage devices, and a magnetic cassette. Alternatively, the program may be stored to a memory combining part or all of those recording media. A plurality of memories may be equipped.

The program may be stored in an attachable storage device accessible via a communication network such as Internet, Intranet, local area network (LAN), wide LAN (WLAN), or storage area network (SAN), or a communication network by combining these networks. The storage device may access the present device through an external port. A separate storage device may access the present device over the communication network.

In the specific embodiments of the present disclosure, the elements included in the disclosure are expressed in a singular or plural form. However, the singular or plural expression is appropriately selected according to a proposed situation for the convenience of explanation and the present disclosure is not limited to a single element or a plurality of elements. The elements expressed in the plural form may be configured as a single element, and the elements expressed in the singular form may be configured as a plurality of elements.

While the present disclosure has been shown and described with reference to various embodiments thereof, it will be understood by those skilled in the art that various changes in form and details may be made therein without departing from the spirit and scope of the present disclosure as defined by the appended claims and their equivalents.

What is claimed is:

1. A wearable device comprising:
   a biometric sensor;
   a communication circuitry;
   an output device; and
   at least one processor operatively coupled with the biometric sensor and the output device, and configured to:
   monitor biometric information of a user over a period of time using the biometric sensor,
   detect initiation of consumption of a food based on detecting a first elevation in a value of the monitored biometric information over the period of time, a start of the first elevation indicating a time at which the consumption is initiated, the first elevation terminating in a peak and followed by a continuous decrease in the value terminating in a valley indicating a digestion completion time, the valley followed by a second elevation in the value, in combination with receiving pre-specified non-biometric information via the communication circuitry,
   determine digestibility of the food by the user by calculating a difference between a maximum value of the monitored biometric information at the peak and a minimum value of the monitored biometric information at the valley before the second elevation in the value, and dividing the calculated difference by a time spanning between the maximum value and the minimum value, and
   provide information of the digestibility, using the output device.

2. The wearable device of claim 1, wherein the maximum value indicates a time at which food consumption ends, and
   wherein the received pre-specified non-biometric information indicating initiation of consumption of the food includes data associated with an electronic payment indicating a payment location pre-associated with food, and a transaction amount associated with a purchase of the food.

3. The wearable device of claim 1, wherein the biometric information comprises a heart rate of the user, and
   wherein the received pre-specified non-biometric information indicating initiation of consumption of the food includes receiving a message associated with an application installed in the wearable device and pre-specified as associated with food.

4. The wearable device of claim 1, wherein the processor is configured to provide, based at least in part on the digestibility, sleep information of the user as at least a portion of the digestibility information, and
   wherein the received pre-specified non-biometric information indicating initiation of consumption of the food includes network information for a network pre-specified as associated with food.

5. A wearable device comprising:
   a housing;
   a display disposed in a first area of the housing;
   one or more sensors electrically connected to one or more terminals contactable to part of a user body through a second area of the housing;
   a communication circuitry;
   a memory storing instructions; and
   one or more processors operably coupled with the memory, the one or more sensors, and the display,
   wherein the memory-stored instructions are executable by the one or more processors to perform operations including:
   monitoring a resting heart rate of the user over a period of time through the one or more sensors,
   detecting initiation of consumption of a food based on detecting a first elevation in a value of the monitored resting heart rate over the period of time, a start of the first elevation indicating a time at which the consumption is initiated, the first elevation terminating in a peak and followed by a continuous decrease in the value terminating in a valley indicating a digestion completion time, the valley followed by a second elevation in the value, in combination with receiving pre-specified non-biometric information via the communication circuitry,
   in response to detecting the initiation of consumption,
   determining a digestibility of the food taken by the user by calculating a difference between a maximum value of the monitored biometric information at the peak and a minimum value of the monitored biometric information at the valley before the second elevation in the value, and dividing the calculated difference by a time spanning between the maximum value and the minimum value, and
   storing the determined digestibility in the memory.

6. The wearable device of claim 5, wherein the maximum value indicates a time at which food consumption ends, and wherein the received non-biometric information indicating initiation of consumption of the food includes data associated with an electronic payment indicating a payment location pre-associated with food, and a transaction amount associated with a purchase of the food.

7. The wearable device of claim 6,
wherein the received non-biometric information indicating initiation of consumption of the food includes receiving a message associated with an application installed in the wearable device and pre-specified as associated with food.

8. The wearable device of claim 5, wherein the operations further comprise:
when monitoring the resting heart rate of the user, determining a sleeping quality of the user based on the digestibility, and
displaying information of the sleeping quality through the display, and
wherein the received non-biometric information indicating initiation of consumption of the food includes network information for a network pre-specified as associated with food.

9. The wearable device of claim 5, further comprising:
a communication interface,
wherein the operations further comprise transmitting the digestibility information to an electronic device associated with the wearable device through the communication interface.

10. The wearable device of claim 5, wherein the operations further comprise receiving food information from an electronic device associated with the wearable device, and
wherein the initiation of consumption of the food is detected based on the food information and the monitored resting heart rate.

11. The wearable device of claim 5, wherein the one or more sensors comprise one or more first sensors configured to obtain movement information of the user, and one or more second sensors configured to obtain the heart rate of the user,
wherein the operations further comprise obtaining, in response to identifying that an amount of user movement obtained through the one or more first sensors falls within a designated range, the resting heart rate through the one or more second sensors.

12. The wearable device of claim 5, wherein the one or more sensors comprise one or more first sensors configured to obtain movement information of the user, and one or more second sensors configured to obtain the heart rate of the user,
wherein the operations further comprise switching, in response to identifying that an amount of the user movement obtained through the one or more first sensors falls within a designated range, an operation state of the one or more second sensors from an idle state to an active state.

13. The wearable device of claim 5, wherein the one or more sensors comprise a photoplethysmography (PPG) sensor and a film disposed over the PPG sensor.

14. The wearable device of claim 5, wherein the operations further comprise displaying an estimated digestion time based on the determined digestibility in a form of a progress bar.

15. The wearable device of claim 14, wherein the operations further comprise transmitting the estimated digestion time information to an external electronic device.

16. An electronic device comprising:
a communication circuitry;
an output device; and
one or more processors operably coupled with the communication circuitry and the output device, the one or more processors configured to:
monitor a resting heart rate of a user from a wearable device associated with the electronic device over a period of time,
detect initiation of consumption of a food based on detecting a first elevation in a value of the monitored resting heart rate over the period of time, a start of the first elevation indicating a time at which the consumption is initiated, the first elevation terminating in a peak and followed by a continuous decrease in the value terminating in a valley indicating a digestion completion time, and the valley followed by second elevation in the value, in combination with receiving non-biometric information via the communication circuitry,
determine digestibility of the food by calculating a difference between a maximum value of the monitored biometric information at the peak and a minimum value of the monitored biometric information at the valley before the second elevation in the value, and dividing the calculated difference by a time spanning between the maximum value and the minimum value, and
provide the determined digestibility via the output device.

17. The electronic device of claim 16, wherein the one or more processors are configured to transmit a signal providing the determined digestibility to the wearable device.

18. The electronic device of claim 16, wherein the determined digestibility further includes user sleeping information.

* * * * *